(12) United States Patent
Schöning et al.

(10) Patent No.: US 9,045,480 B2
(45) Date of Patent: Jun. 2, 2015

(54) STERICALLY HINDERED AMINE LIGHT STABILIZERS

(75) Inventors: Kai-Uwe Schöning, Oberwil (CH); Adriana Edenharter, Zürich (CH); Stefan Hauck, Lampertheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/376,721

(22) PCT Filed: Jun. 1, 2010

(86) PCT No.: PCT/EP2010/057642
§ 371 (c)(1),
(2), (4) Date: Jan. 17, 2012

(87) PCT Pub. No.: WO2010/142576
PCT Pub. Date: Dec. 16, 2010

(65) Prior Publication Data
US 2012/0108709 A1 May 3, 2012

(30) Foreign Application Priority Data

Jun. 8, 2009 (EP) .................................... 09162181

(51) Int. Cl.
| C07D 471/10 | (2006.01) |
| C07D 498/10 | (2006.01) |
| C08K 5/353 | (2006.01) |
| C08K 3/22 | (2006.01) |
| C08K 5/49 | (2006.01) |

(52) U.S. Cl.
CPC ..................................... C07D 471/10 (2013.01)

(58) Field of Classification Search
CPC ........... C07D 471/10; C08K 5/34; C08K 5/35
USPC .................... 524/95, 100; 544/71; 546/18, 19
See application file for complete search history.

(56) References Cited

U.S. PATENT DOCUMENTS

| 3,639,409 A * | 2/1972 | Murayama et al. ............. 546/20 |
| 4,745,192 A * | 5/1988 | Ertl ................................. 546/19 |
| 5,096,950 A * | 3/1992 | Galbo et al. .................... 524/99 |
| 5,633,378 A | 5/1997 | Gaa et al. |
| 6,214,995 B1 | 4/2001 | Stockel |
| 6,265,473 B1 * | 7/2001 | Galbo et al. .................. 524/100 |
| 2007/0014751 A1 * | 1/2007 | Huang et al. ............... 424/78.08 |
| 2012/0108711 A1 | 5/2012 | Sala et al. |

FOREIGN PATENT DOCUMENTS

| DE | 44 23 055 | 1/1996 |
| DE | 100 12 859 | 9/2000 |
| EP | 1 078 929 | 2/2001 |
| EP | 1078929 A2 * | 2/2001 |
| JP | 09 288339 | 11/1997 |
| WO | 2009 049851 | 4/2009 |
| ZA | 20004230 * | 2/2002 |

OTHER PUBLICATIONS

Walter, W., Beyer/Walter Organic Chemistry: A comprehensive degree text and source book, Chichester, West Sussex, England, Albion Publishing Limited (1997), pp. 285.*

Formaggio, F., et al., "Nitroxyl Peptides as Catalysts of Enantioselective Oxidations," Chem. Eur. J., vol. 8, No. 1, pp. 84-93, (2002) XP002551632.

Huang, W., et al., "Unique Behavior of Nitroxide Biradicals in the Controlled Radical Polymerization of Styrene," Macromolecules, vol. 35, No. 6, pp. 2305-2317, (2002) XP002551633.

International Search Report Issued Oct. 5, 2010 in PCT/EP10/057642 Filed Jun. 1, 2010.

U.S. Appl. No. 13/376,849, filed Dec. 8, 2011, Schoening.

* cited by examiner

*Primary Examiner* — Susannah Chung
*Assistant Examiner* — Josephine Chang
(74) *Attorney, Agent, or Firm* — Oblon, McClelland, Maier & Neustadt, L.L.P.

(57) ABSTRACT

The disclosure concerns sterically hindered amine light stabilizers (HALS) with low basicity at the nitrogen atom and high thermal stability. They are characterized by their spiro-substitution in the 4-position of the tetramethylpiperidine ring (Spiro-NOR-HALS). These compounds are useful in stabilizing polymers, especially thermoplastic polyolefins, against the deleterious effects of oxidative, thermal and actinic radiation. The compounds are also useful in stabilizing acid catalyzed and ambient cured coatings systems. They are particularly useful when high processing temperatures are additional required.

15 Claims, No Drawings

STERICALLY HINDERED AMINE LIGHT STABILIZERS

The instant invention pertains to sterically hindered amine light stabilizers (HALS) with low basicity at the nitrogen atom and high thermal stability. These compounds are particularly effective in stabilizing polymers, especially thermoplastic polyolefins, against the deleterious effects of oxidative, thermal and actinic radiation. The compounds are also particularly effective in stabilizing acid catalyzed and ambient cured coatings systems. They are particularly useful when high processing temperatures are additional required.

Conventional HALS (N—H) are excluded from certain applications due to their basic secondary ring nitrogen atom. Examples are acid catalyzed crosslinked polymers or ambient cured coatings.

The present invention solves this problem by providing novel NOR HALS compounds. The compounds prepared can be used as stabilizers for plastics, coatings and home and personal care applications. They are characterized by their spiro-substitution in the 4-position of the tetramethylpiperidine ring (Spiro-NOR-HALS). The corresponding Spiro-NH-HALS are partly items of commerce and described as effective light stabilizers. The 4-spiro substitution has so far not been used in combination with the 1-NOR substitution. Only two compounds are known from DE 4 423 055, namely the N—O-octyl and the N—O-methylbenzyl compounds. Furthermore in WO 2009/049851 spiropiperidine pyrrolidine dione derivatives with a substituted phenyl group attached to the pyrrolidine dione ring have recently been reported and their use as pesticides.

The instant compounds, because of their low basicity and high temperature stability, are of particular value in the stabilization of polyolefins and automotive coating compositions where the activity of the more basic hindered amine stabilizers is significantly reduced because of interaction with the polymer substrate or acid catalysts needed for curing such substrates.

Examples of polyolefin compositions in which the instant compounds are effective include flame retardant polyolefins where acidic residues from the decomposition of the halogenated flame retardants deactivate hindered amines not having the N—OR group, greenhouse films and agricultural mulch films where acidic residues from pesticides or sulfur dioxide treatment interfere with the activity of "normal" hindered amine stabilizers, and in thermoplastic polyolefins where pigment interactions with basic hindered amine stabilizers may occur. Examples of coating compositions in which the instant compounds are effective include melamine crosslinked thermoset acrylic resins, which are cured using strong acids that interact with basic hindered amine stabilizers. The instant compounds are also effective in acrylic alkyd or polyester resins with isocyanate crosslinking agents, and in epoxy resins with carboxylic acid, anhydride, or amine crosslinking agents.

Thus, current compounds are advantageously used in compositions also containing co-stabilizers, flame retardants (e.g. tris(3-bromo-2,2-bis(bromomethyl)propyl)phosphate, decabromodiphenyl oxide, ethylene bis-(tetrabromophthalimide), or ethylene bis-(dibromo-norbornanedicarboximide)), catalysts (e.g. acids like toluene sulfonic acid, metal driers or amines), fillers, fatty acid salts (e.g. calcium stearate) or in agricultural applications wherein pesticides and/or sulfur-containing acids and or metal ions (e.g. iron) come in contact with the stabilized polymer.

One aspect of the invention is a compound of formula (I) or (II)

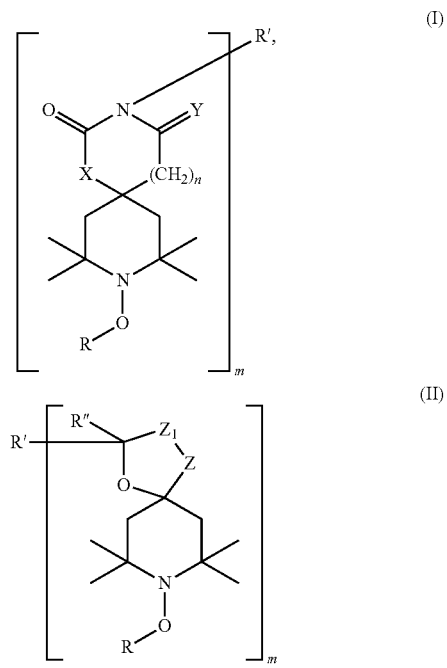

wherein
X and Y are independently NH or O; when n is 0 and X is NH, X has additionally the meaning of N—$C_1$-$C_{20}$alkyl, N—$C_3$-$C_{12}$cycloalkyl, N-phenyl or N—$C_7$-$C_{12}$phenylalkyl;
m is 1 or 2;
n is 0 or 1;
Z is C=O and $Z_1$ is NH; or
Z is NH and $Z_1$ is C=O;
R is $C_1$-$C_{20}$alkyl, $C_3$-$C_{20}$alkenyl, $C_3$-$C_{20}$alkynyl which are unsubstituted or substituted by OH, halogen, $NO_2$, carbonyl or carboxyl; phenyl, $C_7$-$C_{12}$phenylalkyl or $C_3$-$C_{12}$cycloalkyl;
if m is 1
R' and R" are independently H, $C_1$-$C_{20}$alkyl, $C_3$-$C_{20}$alkenyl, $C_3$-$C_{20}$alkynyl which are unsubstituted or substituted by OH, halogen, $NO_2$, carbonyl or carboxyl; phenyl, $C_7$-$C_{12}$phenylalkyl or $C_3$-$C_{12}$cycloalkyl;
with the proviso that if in formula (II) Z is C=O, R is not octyl or methylbenzyl; and
with the proviso that in formula (I) if X is NH, Y is O and n is 0, R' is not H;
if m is 2
R" is H, $C_1$-$C_{20}$alkyl, $C_3$-$C_{20}$alkenyl, $C_3$-$C_{20}$alkynyl which are unsubstituted or substituted by OH, halogen, $NO_2$, carbonyl or carboxyl; phenyl, $C_7$-$C_{12}$phenylalkyl or $C_3$-$C_{12}$cycloalkyl; and
R' $C_1$-$C_{20}$ alkylene, $C_5$-$C_{12}$cycloalkylene, phenylene, $C_1$-$C_4$alkylene-$C_5$-$C_{12}$cycloalkylene-$C_1$-$C_4$alkylene, $C_1$-$C_4$alkylene-phenylene-$C_1$-$C_4$alkylene wherein the phenylene and the $C_5$-$C_{12}$cycloalkyne radicals are unsubstituted or substituted by 1 to 4 $C_1$-$C_4$alkyl groups.

Halogen is fluorine, chlorine, bromine and iodine.

The alkyl radicals in the various substituents may be linear or branched. Examples of alkyl containing 1 to 20 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

$C_3$-$C_{12}$cycloalkyl is typically cyclopropyl, cyclopentyl, methylcyclopentyl, dimethylcyclopentyl, cyclohexyl, methylcyclohexyl.

$C_3$-$C_{20}$alkenyl is, for example, propenyl, butenyl, pentenyl, hexenyl, heptenyl, octenyl, dode-cenyl including their isomers.

$C_7$-$C_{12}$phenylalkyl is for example benzyl, phenylpropyl, α,α-dimethylbenzyl or α-methyl-benzyl.

$C_3$-$C_{20}$alkynyl is preferably propargyl.

Alkyl substituted by —OH is typically 2-hydroxyethyl, 2-hydroxypropyl or 2-hydroxybutyl.

For example the compounds are of formula (Id), (Id'), (Ie), (Ie'), (If), (If'), (IIa) or (IIb)

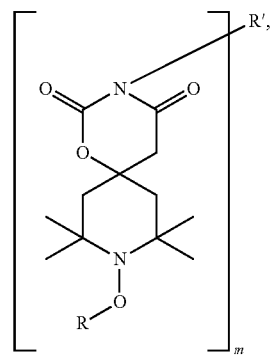
(Id)

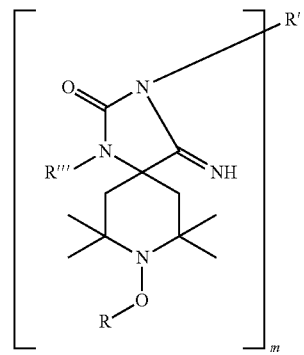
(Id')

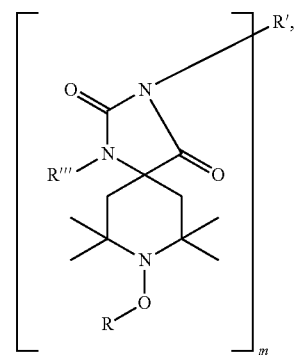
(Ie)

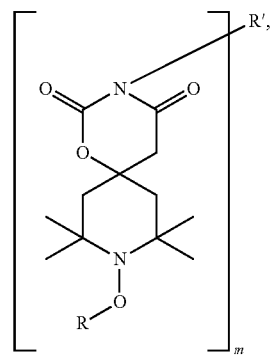
(Ie')

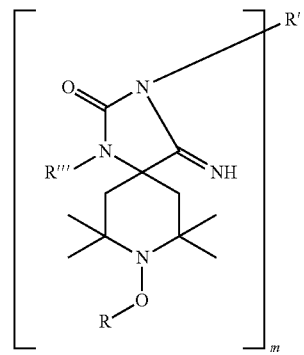
(If)

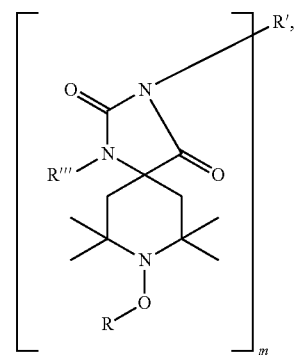
(If')

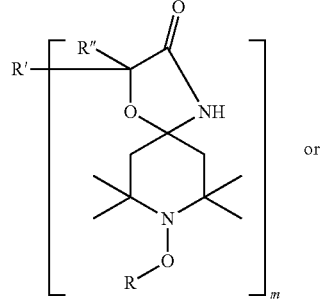
(IIa)

or

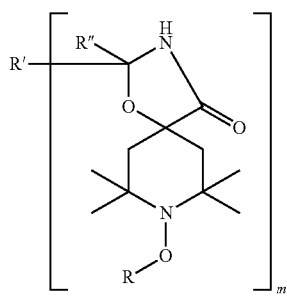

(IIb)

wherein m and the substituents R, R' and R" have the meaning as defined above, R'" is H, $C_1$-$C_{20}$alkyl, $C_3$-$C_{12}$cycloalkyl, phenyl or $C_7$-$C_{12}$phenylalkyl;

and if m is 1 with the proviso that in formula (IIb), R is not octyl or methylbenzyl; and in formula (If'), R' is not H when R'" is H.

For instance in the above formulae R is $C_1$-$C_{20}$alkyl, $C_3$-$C_{20}$alkenyl, $C_3$-$C_{20}$alkynyl which are unsubstituted or substituted by OH, carbonyl or carboxyl; phenyl, $C_7$-$C_9$phenylalkyl or $C_5$-$C_8$cycloalkyl;

R'" is H, $C_1$-$C_{20}$alkyl, $C_3$-$C_{12}$cycloalkyl, phenyl or $C_7$-$C_{12}$phenylalkyl;

if m is 1

R' and R" are independently H, $C_1$-$C_{20}$alkyl, $C_3$-$C_{20}$alkenyl, $C_3$-$C_{20}$alkynyl which are unsubstituted or substituted by OH, carbonyl or carboxyl; phenyl, $C_7$-$C_9$phenylalkyl or $C_5$-$C_8$cycloalkyl;

if m is 2

R' $C_1$-$C_{20}$ alkylene, $C_5$-$C_{12}$cycloalkylene, phenylene, $C_1$-$C_4$alkylene-$C_5$-$C_{12}$cycloalkylene-$C_1$-$C_4$alkylene, $C_1$-$C_4$alkylene-phenylene-$C_1$-$C_4$alkylene wherein the phenylene and the $C_5$-$C_{12}$cycloalkyne radicals are unsubstituted or substituted by 1 to 4 $C_1$-$C_4$alkyl groups;

R" is H, $C_1$-$C_{20}$alkyl, $C_3$-$C_{20}$alkenyl, $C_3$-$C_{20}$alkynyl which are unsubstituted or substituted by OH, carbonyl or carboxyl; phenyl, $C_7$-$C_9$phenylalkyl or $C_5$-$C_8$cycloalkyl.

Preferably R is $C_1$-$C_{20}$alkyl, phenyl, $C_7$-$C_8$phenylalkyl or $C_5$-$C_6$cycloalkyl;

R'" is H or $C_1$-$C_{20}$alkyl;

if m is 1

R' and R" are independently H, $C_1$-$C_{20}$alkyl, phenyl, $C_7$-$C_8$phenylalkyl or $C_5$-$C_6$cycloalkyl;

if m is 2

R' $C_1$-$C_{20}$ alkylene, $C_5$-$C_{12}$cycloalkylene, phenylene, $C_1$-$C_4$alkylene-$C_5$-$C_{12}$cycloalkylene-$C_1$-$C_4$alkylene, $C_1$-$C_4$alkylene-phenylene-$C_1$-$C_4$alkylene wherein the phenylene and the $C_5$-$C_{12}$cycloalkyne radicals are unsubstituted or substituted by 1 to 4 $C_1$-$C_4$alkyl groups; R" is H, $C_1$-$C_{20}$alkyl, phenyl, $C_7$-$C_8$phenylalkyl or $C_5$-$C_6$cycloalkyl.

In general it is preferred that in the above formulae m is 1.

Particularly suitable individual compounds are the following.

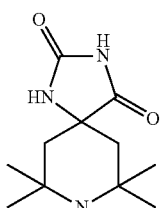

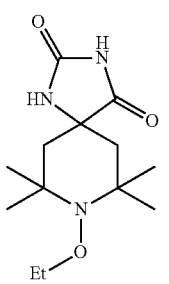

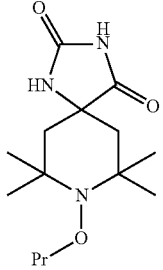

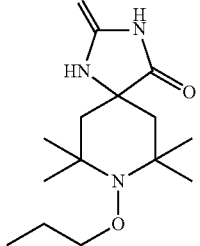

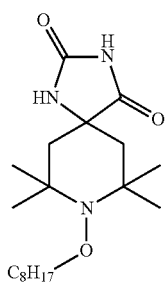

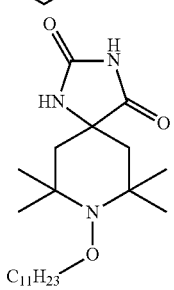

-continued
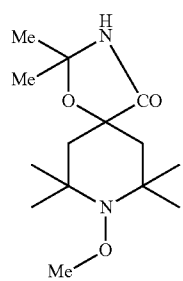 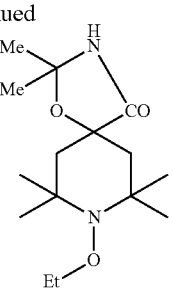
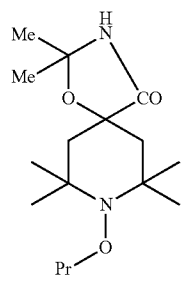 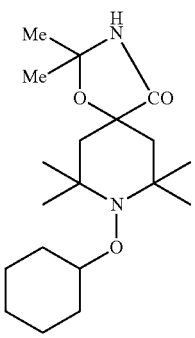
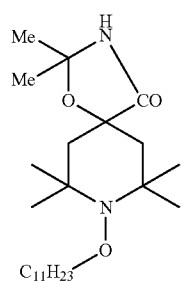 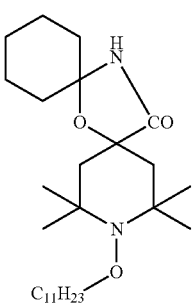
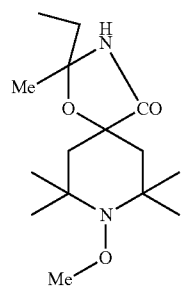 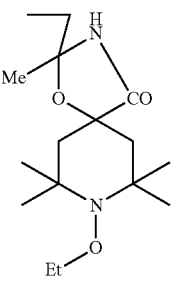
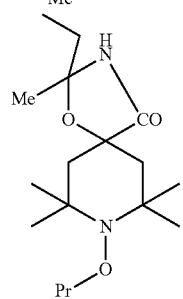 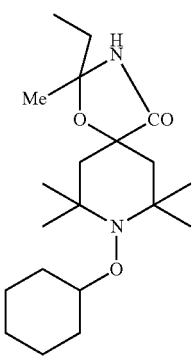

-continued
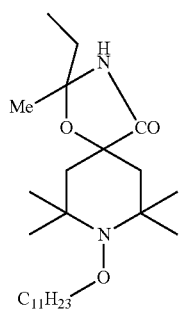
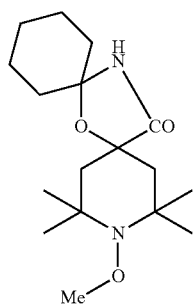
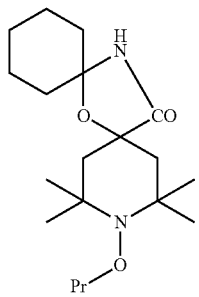
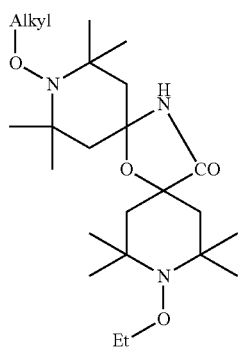
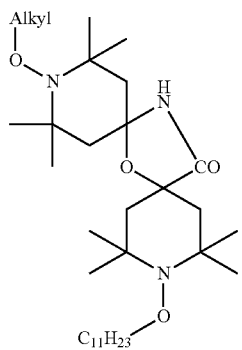
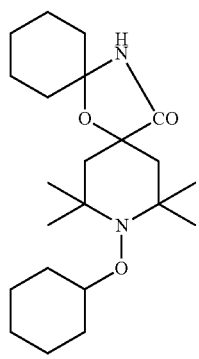
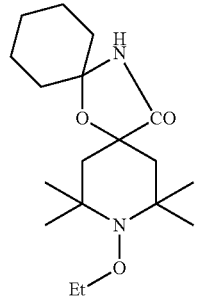
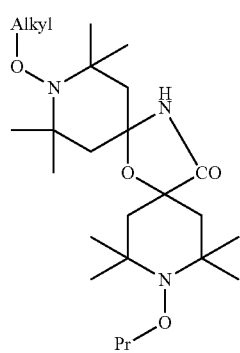
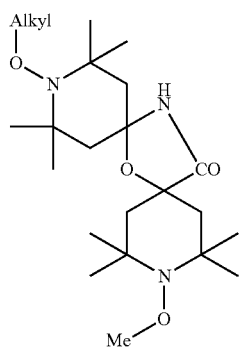
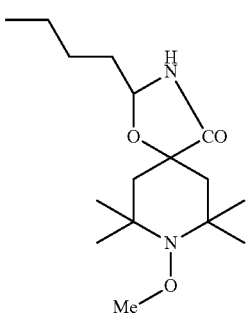

-continued
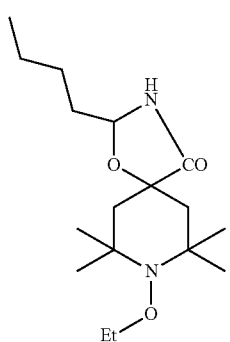 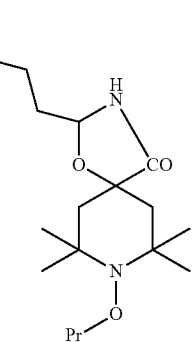
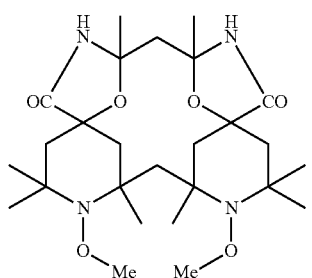 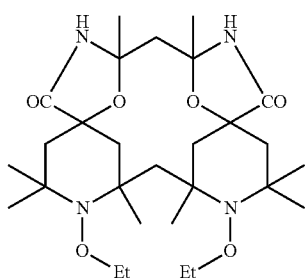
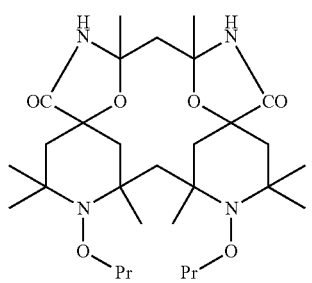 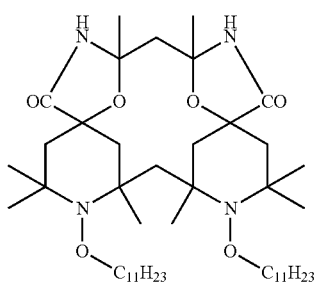
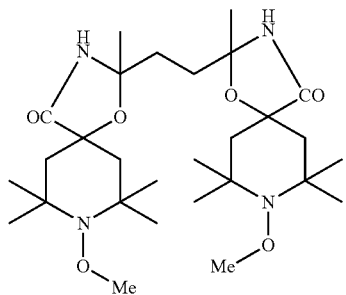 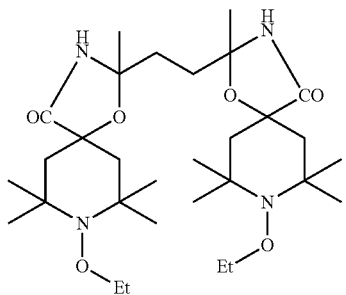
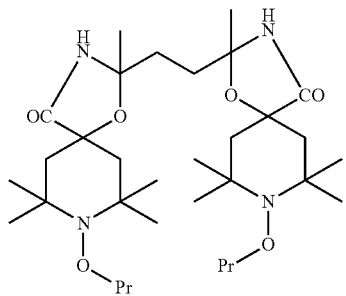 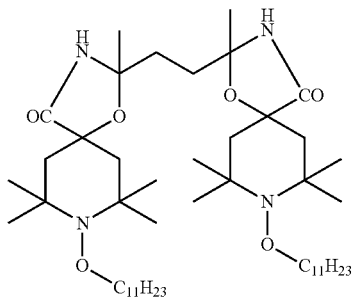

-continued
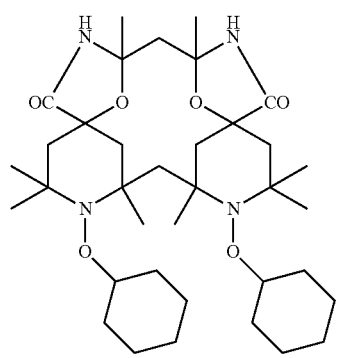
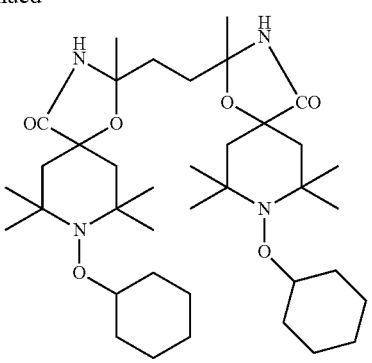
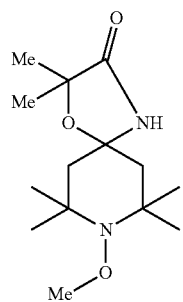
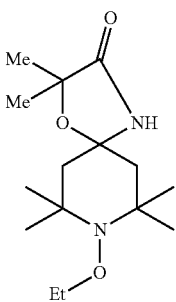
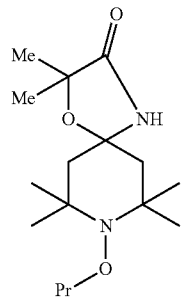
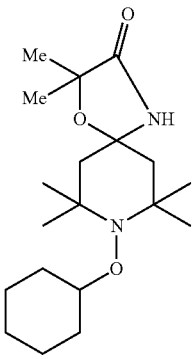
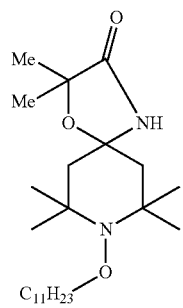
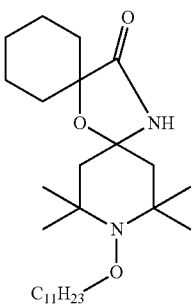
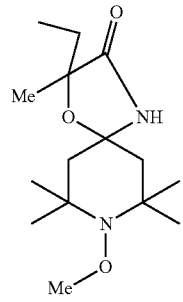
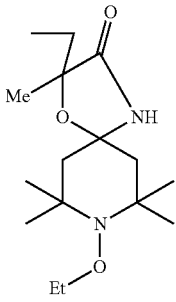

-continued
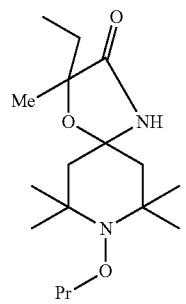
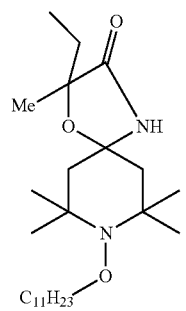
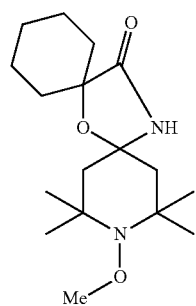
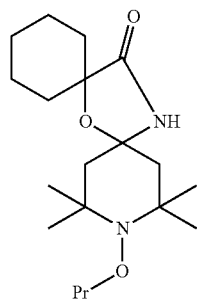
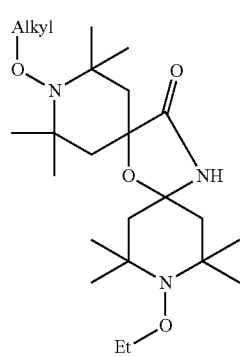
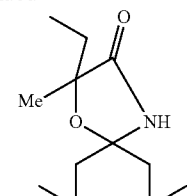
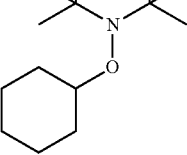
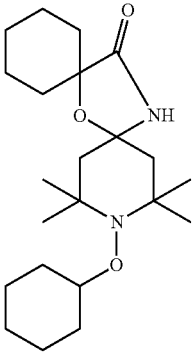
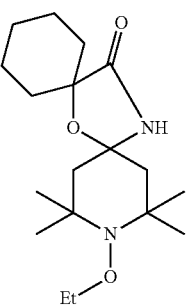
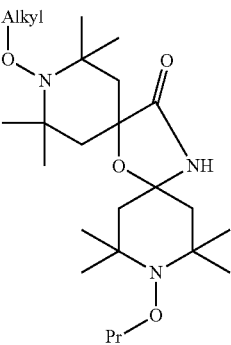
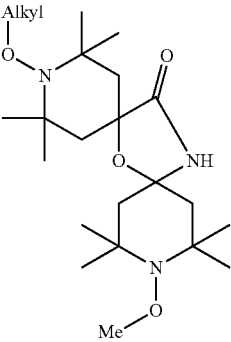

-continued
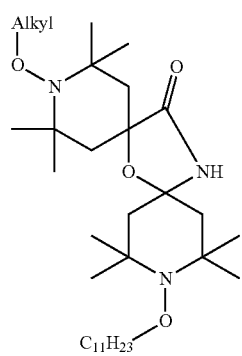
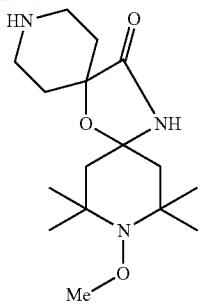
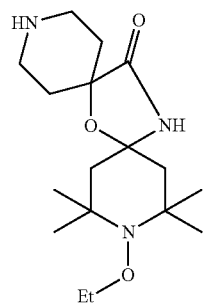
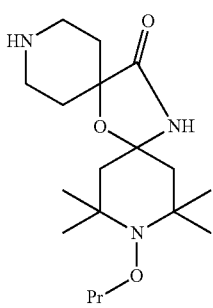
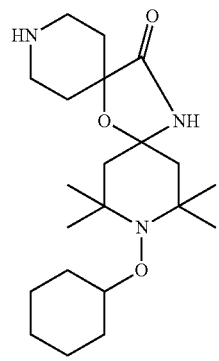
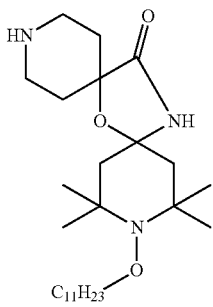
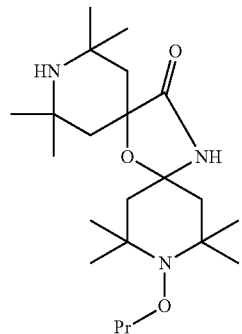
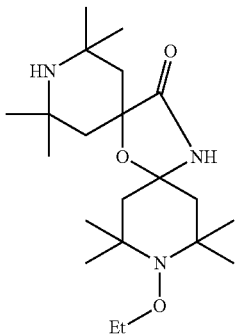
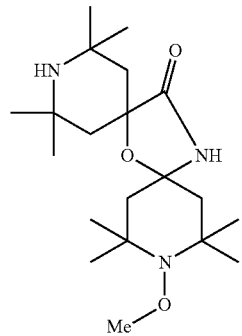
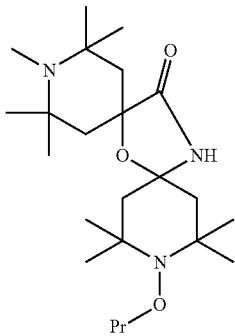

-continued
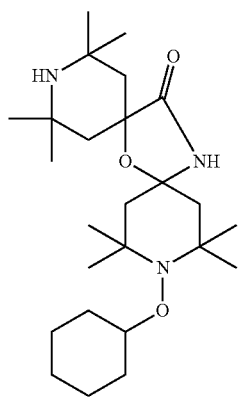
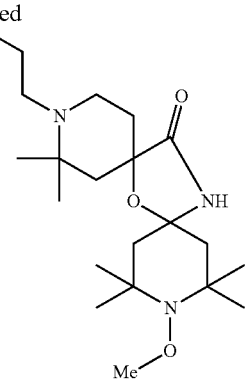
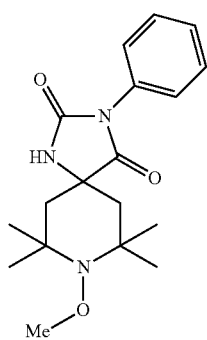
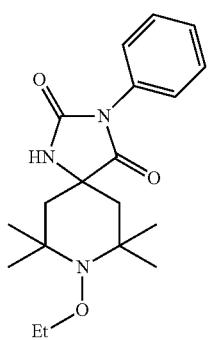
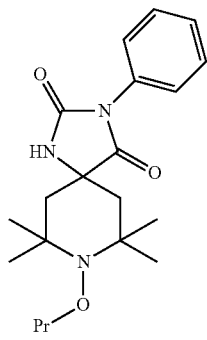
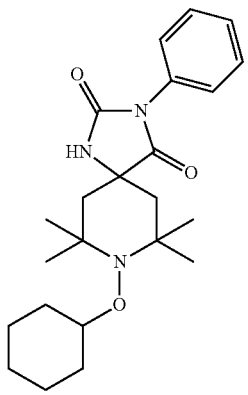
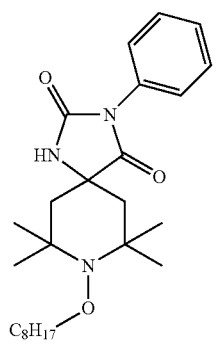
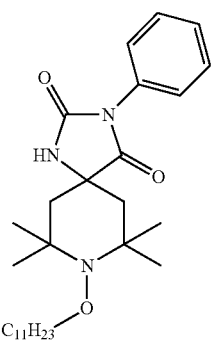

-continued
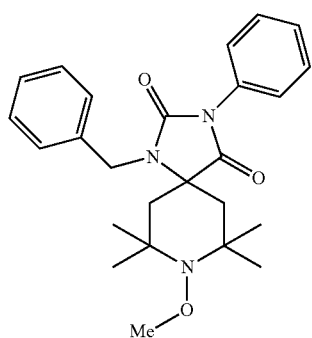
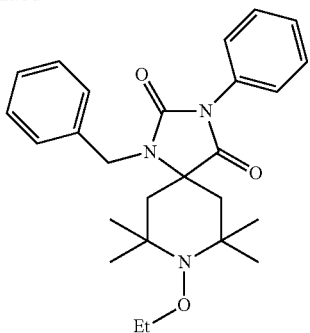
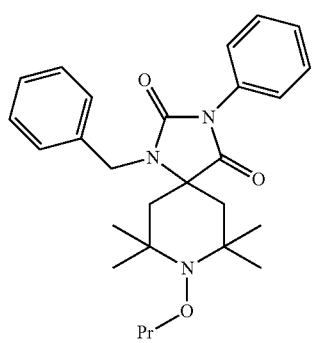
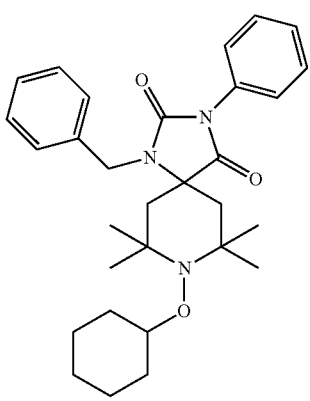
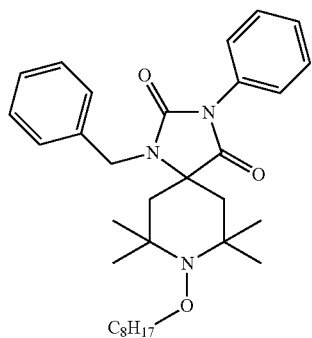
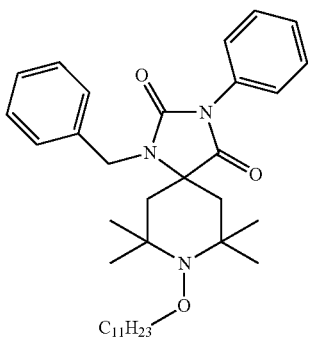
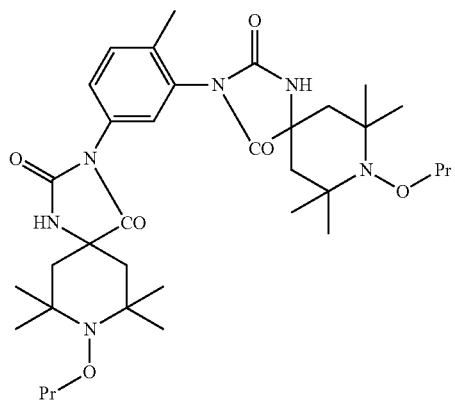
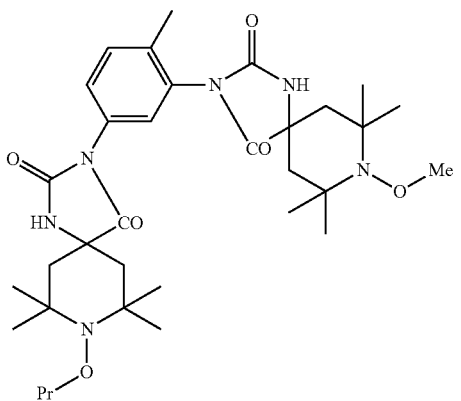
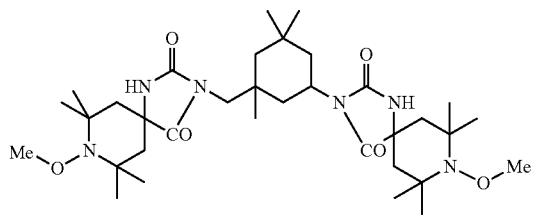
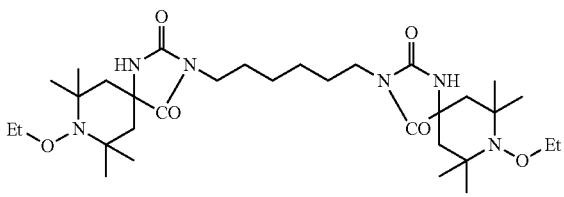

-continued
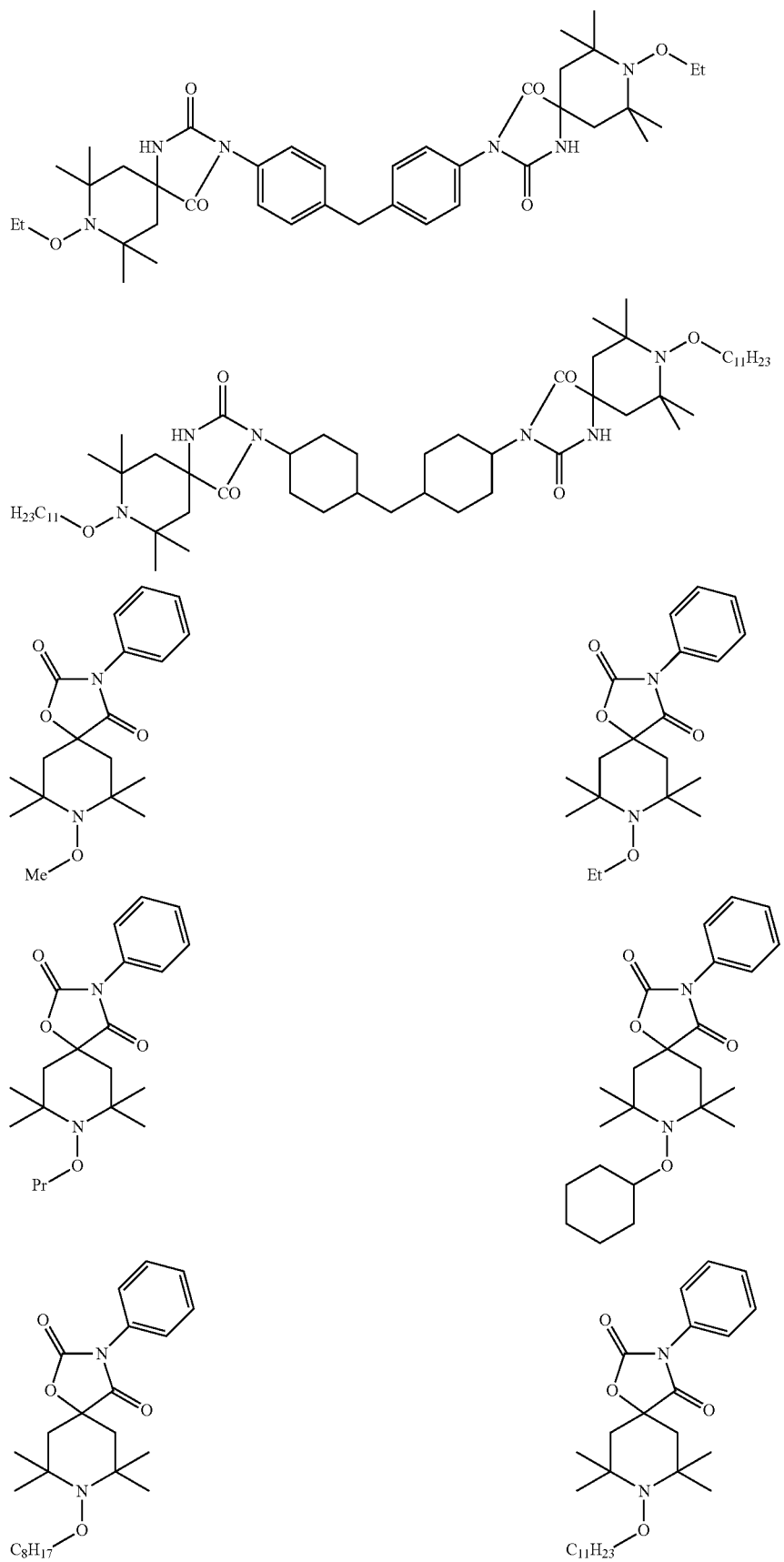

25
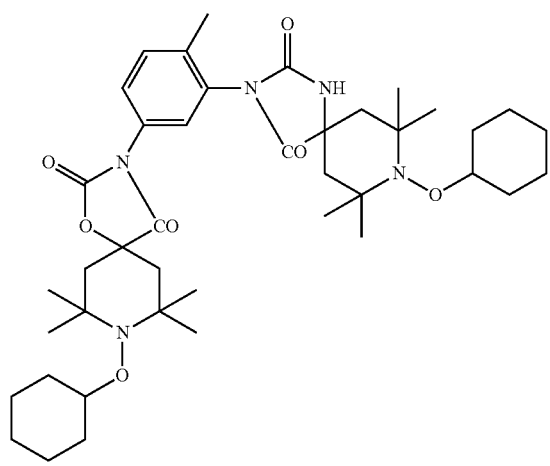
26
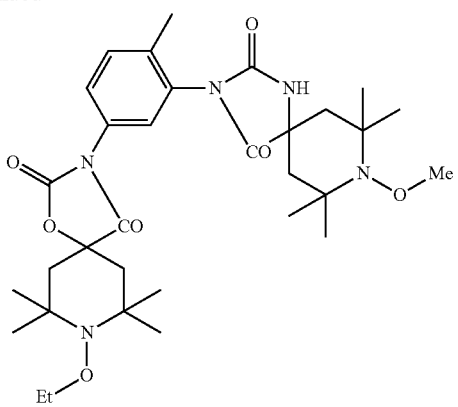
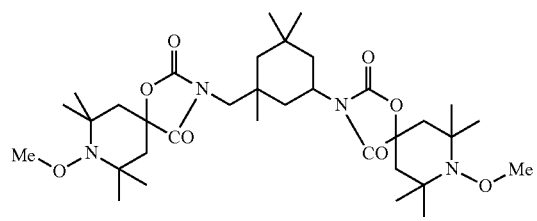
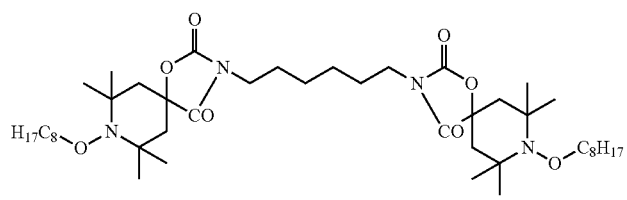
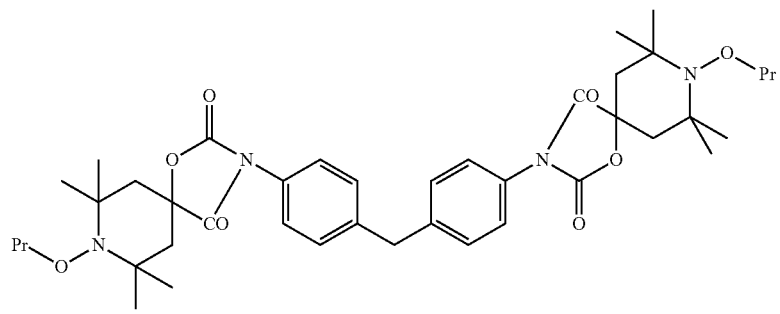
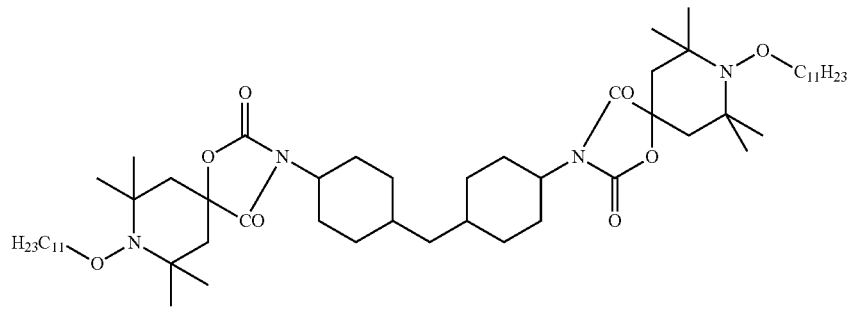
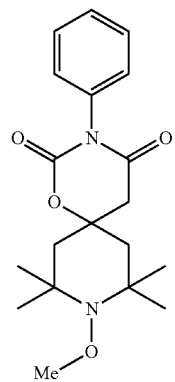
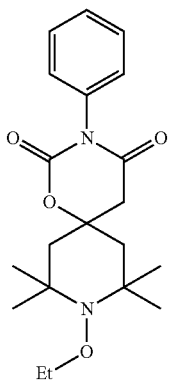

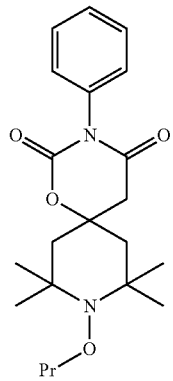
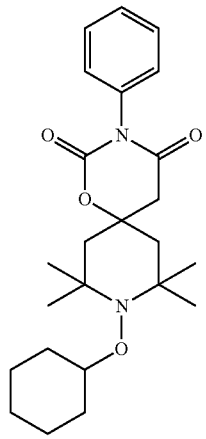
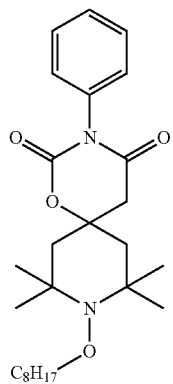
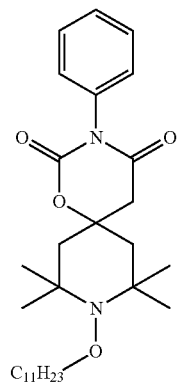
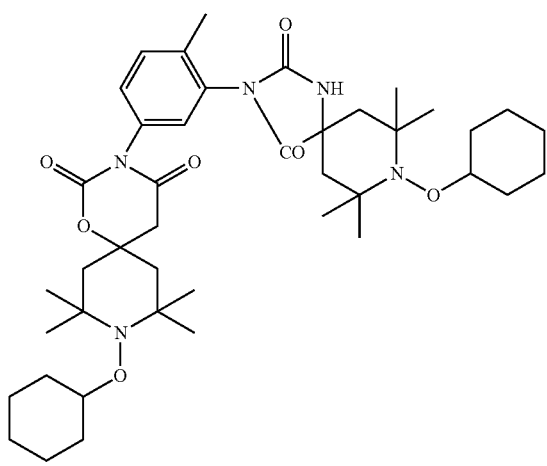
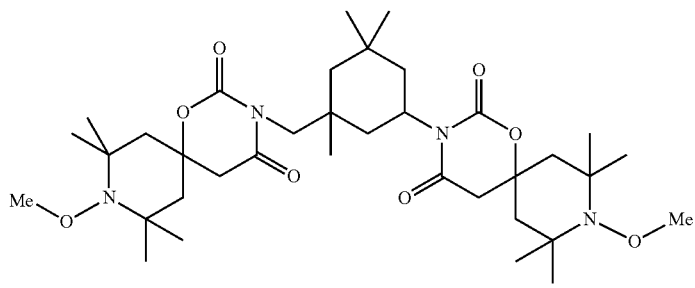

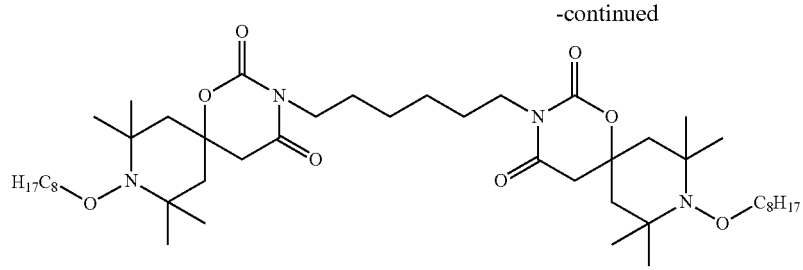

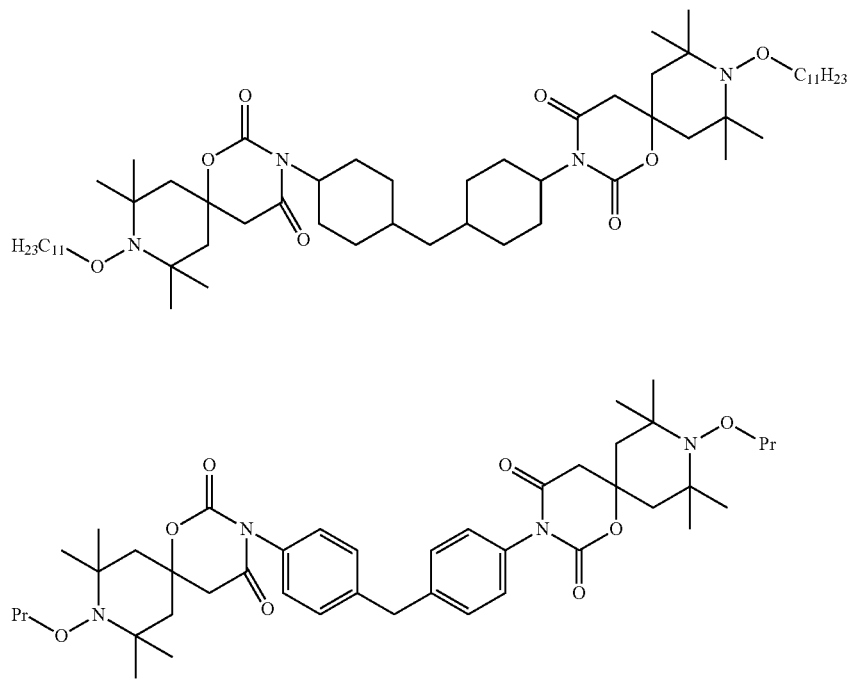

The preparation of the compounds of formulae (I), (II), (Id), (Id'), (Ie), (Ie'), (If), (If'), (IIa) or (IIb) starts from 4-oxo-tetramethylpiperidine which can be oxidized to the nitroxide radical and then reacted to the corresponding N—O—R compound of formula (O)

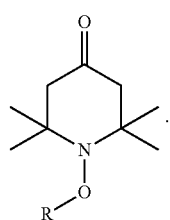

(O)

The preparation and use of N—O—R compounds is, for example, described in U.S. Pat. No. 5,004,770 and U.S. Pat. No. 5,096,950.

The following scheme explains the individual steps of the preparation procedure starting from a compound of formula (O).

Reaction Scheme

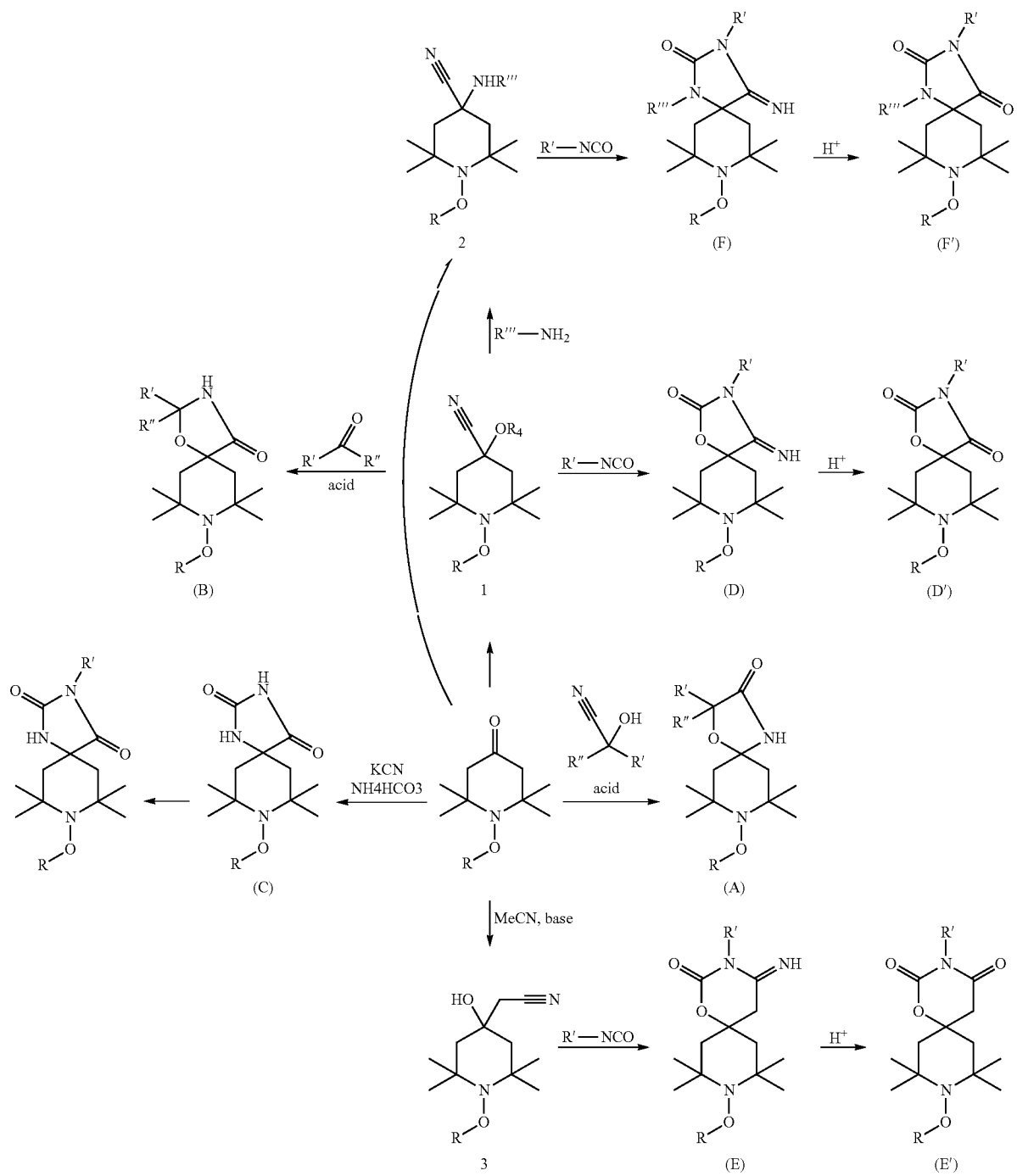

For reasons of clarity only compounds wherein m is 1 are presented. The substituents R, R', R" and R''' are as defined above.

Formation of Cyanohydrines of Formula (1)

a) Cyanohydrines can be formed as described, for example, by Robert J. H. Gregory, Chem. Rev., 1999, 99 (12), pp 3649-3682 by a) either reacting a 4-oxo-2,2,6,6-tetramethylpiperidine derivative, compound of formula (O), with HCN gas, or a HCN-liberating source such as combinations of cyanides (NaCN, KCN) and acids (HCl, $H_2SO_4$, $NaHSO_4$) as described in EP 1078929, FR 1582525, DE 2606026 or DE 2834962.

b) Reacting a 4-oxo-2,2,6,6-tetramethylpiperidine or derivative, compound of formula (O), with acetone cyanohydrine in the presence of a base or Lewis-acid as described, e.g., Journal of Medicinal Chemistry (2005), 48(20), 6379-6385; Chemistry Letters (1993), 2, 375-8; Chemistry Letters (1991), (1), 145-8; Chemische Berichte (1990), 123(4), 887-

93; Journal of Organic Chemistry (1987), 52(12), 2602-4 and Australian Journal of Chemistry (1979), 32(8), 1805-17.

c) Reacting a 4-oxo-2,2,6,6-tetramethylpiperidine or derivative, compound of formula (O), with a HCN source in the presence of a suitable enzyme as described in "Biocatalysis in the enantioselective formation of chiral cyanohydrins, valuable building blocks in organic synthesis", Stereoselective Biocatalysis (2000), 289-320.

d) Reacting a 4-oxo-2,2,6,6-tetramethylpiperidine or derivative, compound of formula (O), with a latent HCN source such as trimethylsilyl cyanide in the presence of a suitable catalyst (e.g. $ZnI_2$, potassium p-toluenesulfinate, mesoporous Al-MCM-41 catalyst, $SmI_2$, Ti(IV) complex, $Fe(Cp)_2PF_6$, benzyltriphenylphosphonium chloride, iodine, $NbF_5$, aluminum phthalocyanine, amiono acids, polyoxometalates, tetraalkylammonium cyanides, tetrabutylammonium phthalimide-N-oxyl, polyaniline-supported Sc, In, Pd, Os, and Re catalysts, N-octyldihydroimidazolium hydroxide, iron(III) triflate, N-heterocyclic carbenes, 1,1,3,3-tetramethylguanidine, $P(RNCH_2CH_2)_3N$, vanadyl triflate, dodecatungestophosphoric acid ($H_3PW_{12}O_{40}$), $Et_3N$, $K_2CO_3$, phenolic N-oxide, cesium fluoride, $LiClO_4$, iodine, $Cu(OTf)_2$, ytterbium tricyanide or neutral Tr-nucleophiles, such as 1-methoxy-2-methyl-1-(trimethylsiloxy)propene.

In general, it is preferred to use HCN gas under pressure or a cyanide in combination with an acid to prepare the cyanohydrines or trimethylsilyl cyanide and a catalyst to prepare the O-protected cyanohydrine intermediates.

Formation of Compounds of Formula (2)

Compounds of formula (2) can be prepared through the reaction of cyanohydrines with amines or ammonia or through the reaction of a compound of formula (O) (ketones) with amines/ammonia and a HCN/cyanide source. These reactions are in principal known and described by several authors. Examples are given e.g. in (a) Mori, A.; Inoue, S. in Comprehensive Asymmetric Catalysis, Vol. II; Jacobsen, E. N.; Pfaltz, A.; Yamamoto, H., Eds.; Springer: Heidelberg, 1999, 983. (b) Enders, D.; Shilvock, J. P. Chem. Soc. Rev. 2000, 29, 359. (c) Yet, L. Angew. Chem. Int. Ed. 2001, 40, 875. (d) Groger, H. Chem. Rev. 2003, 103, 2795. (e) Spino, C. Angew. Chem. Int. Ed. 2004, 43, 1764. (f) Vachal, P.; Jacobsen, E. N. in Comprehensive Asymmetric Catalysis, Suppl. 1; Jacobsen, E. N.; Pfaltz, A.; Yamamoto, H., Eds.; Springer: Berlin, 2004, 117.

Useful amines and diamines are ammonia, methylamine, propylamine, butylamine, hexylamine, octylamine, cyclohexylamine, benzylamine, anilin, naphthylamine, 2-ethylhexylamine, toluidine, phenylethylamine, 1,2-propylendiamin, 1,3-propandiamine, 2,6-xylidine, 2-aminoethylethylene urea, 3,3'-dimethyl-4,4'-diaminodicyclohexylmethane, 4,4'-diaminodicyclohexylmethane, $C_{11}$-neodiamine, cyclohexylmethylamin, ethylendiamine, isophorondiamine, isopropylamine, 2,2-dimethyl 1,3-propandiamine, tridecylamine, tert.-butylamin, Formation of Compounds of Formula (3)

Compounds of formula (3) can for instance be prepared according to WO2008073067 and under the conditions described therein. The addition of acetonitrile to a compound of formula (O) can be carried out from –80° C. to room temperature, preferably between –80° C. and –50° C. Typical bases for the deprotonation of acetonitrile are n-butyllithium, sec. butyllithium or tert-butyllithium, sodium amide, lithium amide, sodium hydride; n-butyllithium is preferred. The reaction is carried out in aprotic solvents such as THF, dioxane, diethylether, hexane, toluene; preferentially in THF.

Suprisingly, it has been found that certain N-alkoxyamines with specific heterocyclic moieties can be prepared even under strongly acidic conditions, i.e. in the presence of strong mineral acids, such as the compounds A, B, D', E', F'—although the cleavage of N-alkoxyamine ethers in acidic environments (under acidic conditions) is frequently described in the chemical literature, for instance in Bioorganic & Medicinal Chemistry Letters (2008), 18(1), 409-413.

Compounds of formula (A) can be prepared according to DE 3541665, DE 3541664, DE 3524542, DE 3104294 or DE.

Typical cyanohydrines for this transformation are acetone cyanohydrine, 1-hydroxycyclohexanecarbonitrile, 2-hydroxy-2-methylbutyronitrile, benzophenone cyano-hydrine, 1-hydroxycyclopentanecarbonitrile, cycloheptanecarbonitrile, 1-azabicyclo[2.2.2]-octane-3-carbonitrile, 2,2,6,6-tetramethyl-4-hydroxy-4-cyanopiperidine, 1-alkyl, 2,2,6,6-tetramethyl-4-hydroxy-4-cyanopiperidine or 2-Ethyl-2-hydroxybutanenitrile. Typically the reaction temperature is between –20° to 150° C., preferably 0° to 110° C. and more preferably from 50 to 80° C.

The reaction is carried out under acidic conditions (using e.g. HCl, $H_2SO_4$, $H_3PO_4$) in inert solvents (e.g. acetic acid). Most preferentially, acetic acid is used as solvent.

The reaction is carried out at atmospheric pressure or from 1-100 bar (autoklave). For example from 1-20 bar, preferably 1 bar.

Typical reaction times vary from 1 hour to 48 hours.

Compounds (B) can be prepared according to EP 1078929, DE 2606026, DE 2834962, or EP 17617 or starting from 0-protected cyanohydrines (compound (1), $R^4$=Si(Alkyl, Aryl)$_3$). Preferentially, $R^4$ is $SiMe_3$.

Useful mono aldehydes and ketones are, for example formaldehyde, acetaldehyde propionaldehyde, butyraldehyde, isobutyraldehyde, valeraldehyde, capronaldehyde, pivalaldehyde, benzaldehyde, naphthylaldehyde, toluylaldehyde, anisaldehyde, salicylaldehyde, acetone, pinakolone, methylethylketone, diethylketones, dipropylketone, methylbutylketone, acetophenone, triacetoneamine, N-alkyl triacetoneamine, 4-oxo-tetramethyl-N-alkoxyamines (4-Oxo-NORs), 4-piperidone, dodecanone, cycloheptanone, cyclopentanone, benzophenone or cyclohexylketone.

Useful dialdehydes and diketones are, for example, glyoxal, malondialdehyde, succindialdehyde, glutar dialdehyde, phthalaldehyde, isophthalaldehyde, terephthalaldehyde, methylglyoxal, hexane-2,5-dione, dimedone, diacetyl, benzyl or acetylaceton.

Typically the reaction temperature is between –20° to 150° C., preferably 0° to 110° C. and more preferably from 50 to 80° C.

The reaction is carried out under acidic conditions (using e.g. HCl, $H_2SO_4$, $H_3PO_4$) in inert solvents (e.g. acetic acid). Most preferentially, acetic acid is used as solvent.

The reaction is carried out at atmospheric pressure or from 1-100 bar (autoklave). For example from 1-20 bar, preferably 1 bar.

Typical reaction times vary from 1 hour to 48 hours.

Compounds of formula (C, D, D', E, E', F, F') can be prepared as indicated below.

Compounds of formula (C, F, F') can be prepared by means of the Bucherer-Bergs reaction (Li, Jie Jack. Bucherer—Bergs reaction, Name Reactions in Heterocyclic Chemistry (2005), 266-274) starting from 4-oxo-N-alkoxyamines to prepare unsubstituted hydantoines or from a compound of formula (2) to prepare substituted ones. Further methods are described in "Recent developments in hydantoin chemistry, a review", Organic Preparations and Procedures International (2004), 36(5), 391-443; FR 1582525 or DE 2233121.

Compounds of formula (E, E') can be prepared according to JP 47049068 or FR 1582525

Compounds of formula (D, D') can be prepared according to JP 47049068 or FR 1582525 starting from a compound of formula (1). If a protected form of the cyanohydrine is used (e.g. a trimethylsilyl ether), it is beneficial to add a catalyst which facilitates the deprotection of the hydroxy group. Such a catalyst can be a fluoride source (e.g. tetrabutylammonium fluoride, potassium fluoride, $H_2SiF_6$) or a Lewis-acid (e.g. $FeCl_3$, $BF_3*Et_2O$) or any other of the state-of-the-art reagents for the deprotection of silyl ethers, for instance mentioned in P. G. M. Wuts, T. W. Greene "Greene's protecting groups in organic synthesis", 4 Ed, Wiley-Interscience, 2007, p. 165-221.

Typical monoisocyanates are, for example, $C_1$-$C_{12}$alkylisocyanate, such as methylisocyanate, phenylisocyanate, naphthylisocyanate or cyclohexanisocyanate.

Typical diisocyanates are widely item of commerce and are, for example, toluenediiso-cyanate, 4,4'-methylenbis (phenylisocyanate), hexamethylenediisocyanate, isophorondiisocyanate.

The individual reaction steps are, for example, carried out under the conditions outlined below.

Typically the reaction temperature is between 0° to 150° C., preferably 25° to 130° C. and more preferably from 25 to 110° C.

When a catalyst is used it is typically used in an amount of 0.001-25 weight %, for example 0.05-10% by weight and preferably 0.1-5% by weight, based on the weight of the ketone. If a reagent for the deprotection of cyanohydrine TMS ethers is used, it is used in amounts of 1-5 equiv., preferable 1-3 equiv. and more preferably 1-1.5 equiv. with regard to the amount of ether.

The reaction is carried out at atmospheric pressure or from 1-100 bar (autoklave). For example from 1-20 bar, preferably 1 bar.

Typical reaction times vary from 1 hour to 48 hours.

Instead or in addition to heating, the reactions may be performed under microwave or ultrasound conditions.

Possible solvents are aprotic, polar and apolar solvents aromatic or aliphatic solvents, ethers or ketones. Examples are toluene, xylene, ionic liquids, hexane, methyl-tert-butylether, dioxan, chlorinated solvents (e.g. methylene chloride, 1,2-dichloroethane, chloroform, chlorobenzene), dimethylformamide (DMF) or polyethyleneglycole (PEG). It is also possible to carry out the reactions without any solvent.

A further aspect of the invention is a process for the preparation of a compound of formulae (I), (II), (Id), (Id'), (Ie), (Ie'), (If), (If'), (IIa) or (IIb), as described above, comprising the steps a) reacting a compound of formula (O)

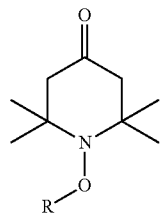

(O)

with HCN or a precursor of HCN or with a compound of formula

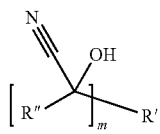

in the presence of a Lewis base to yield a compound of formula (1)

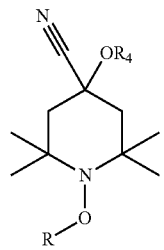

(1)

wherein $R_4$ is H or $Si(CH_3)_3$; and b) reacting a compound of formula (1) with an amine of formula R'''—$NH_2$ to yield a compound of formula (2)

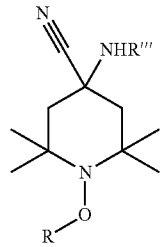

(2)

wherein R''' is H, $C_1$-$C_{20}$alkyl, $C_3$-$C_{12}$cycloalkyl, phenyl or $C_7$-$C_{12}$phenylalkyl or reacting a compound of formula (O) with HCN or a precursor of HCN in the presence of an amine or ammonia; or c) reacting a compound of formula (O) with $CH_3CN$ and a base to yield a compound of formula (3)

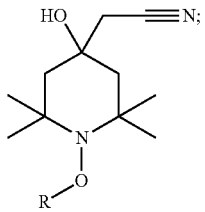

(3)

or d) reacting a compound of formula (O) with a compound of formula

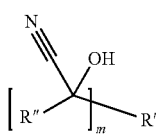

to yield a compound of formula (IIa); and in a further step e) reacting the compound of formula (1) with an aldehyd, dialdehyde, ketone or diketone of formula

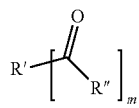

to yield a compound of formula (IIb); or reacting the compound of formula (1) with an isocyanate or diisocyanate of formula R'—[NCO]$_m$ to yield a compound of formula (Id), (Id'); or f) reacting a compound of formula (2) with an isocyanate of formula R'—[NCO]$_m$ to yield a compound of formula (If), (If'); or g) reacting a compound of formula (3) with an isocyanate of formula R'—[NCO]$_m$ to yield a compound of formula (Ie), (Ie')

wherein R, R', R" and m are as defined above.

The individual process steps are typically carried out at a temperature from −20° C. to 100° C., preferably 0 to 60° C. and more preferably from 0° to 25° C.

Typically the process steps are carried out at a pressure of from atmospheric pressure to 100 bar, for example from 1-20 bar, preferably at 1 bar.

Also an aspect of the invention is a composition which comprises
  (a) an organic polymer subject to the adverse effects of heat, oxygen and light, and
  (b) one or more compounds according to formula (I) or (II) or of formulae (Id), (Id'), (Ie), (I'), (If), (If'), (IIa) or (IIb) as described above.

The compounds of the invention are, for example, present in an amount of from 0.01 to 5%, preferably from 0.025 to 2%, and especially from 0.1 to 1%, based on the weight of the organic polymer.

Suitable organic polymers are mentioned below.

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
  a) radical polymerisation (normally under high pressure and at elevated temperature).
  b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups II, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is gene-rated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimides, polyesterimides, polyhydantoins and polybenzimidazoles.

18. Polyesters derived from dicarboxylic acids and diols and/or from hydroxycarboxylic acids or the corresponding lactones or lactides, for example polyethylene terephthalate, polybutylene terephthalate, poly-1,4-dimethylolcyclohexane terephthalate, polyalkylene naphthalate and polyhydroxybenzoates as well as copolyether esters derived from hydroxyl-terminated polyethers, and also polyesters modified with polycarbonates or MBS. Copolyesters may comprise, for example—but are not limited to—polybutylenesuccinate/terephtalate, polybutyleneadipate/terephthalate, polytetramethyleneadipate/terephthalate, polybutylensuccinate/-adipate, polybutylensuccinate/carbonate, poly-3-hydroxybutyrate/octanoate copolymer, poly-3-hydroxybutyrate/hexanoate/decanoate terpolymer. Furthermore, aliphatic polyesters may comprise, for example—but are not limited to—the class of poly(hydroxyalkanoates), in particular, poly(propiolactone), poly(butyrolactone), poly(pivalolactone), poly(valerolactone) and poly(caprolactone), polyethylenesuccinate, polypropylenesuccinate, polybutylenesuccinate, polyhexamethylenesuccinate, polyethyleneadipate, polypropyleneadipate, polybutyleneadipate, polyhexamethyleneadipate, polyethyleneoxalate, polypropyleneoxalate, polybutylene-oxalate, polyhexamethyleneoxalate, polyethylenesebacate, polypropylenesebacate, polybutylenesebacate and polylactic acid (PLA) as well as corresponding polyesters modified with polycarbonates or MBS. The term "polylactic acid (PLA)" designates a homopolymer of preferably poly-L-lactide and any of its blends or alloys with other polymers; a co-polymer of lactic acid or lactide with other monomers, such as hydroxy-carboxylic acids, like for example glycolic acid, 3-hydroxy-butyric acid, 4-hydroxy-butyric acid, 4-hydroxy-valeric acid, 5-hydroxyvaleric acid, 6-hydroxy-caproic acid and cyclic forms thereof; the terms "lactic acid" or "lactide" include L-lactic acid, D-lactic acid, mixtures and dimers thereof, i.e. L-lactide, D-lactide, meso-lacide and any mixtures thereof.

19. Polycarbonates and polyester carbonates.
20. Polyketones.
21. Polysulfones, polyether sulfones and polyether ketones.
22. Crosslinked polymers derived from aldehydes on the one hand and phenols, ureas and melamines on the other hand, such as phenol/formaldehyde resins, urea/formaldehyde resins and melamine/formaldehyde resins.
23. Drying and non-drying alkyd resins.
24. Unsaturated polyester resins derived from copolyesters of saturated and unsaturated dicarboxylic acids with polyhydric alcohols and vinyl compounds as crosslinking agents, and also halogen-containing modifications thereof of low flammability.
25. Crosslinkable acrylic resins derived from substituted acrylates, for example epoxy acrylates, urethane acrylates or polyester acrylates.
26. Alkyd resins, polyester resins and acrylate resins crosslinked with melamine resins, urea resins, isocyanates, isocyanurates, polyisocyanates or epoxy resins.
27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Preferred is a thermoplastic organic polymer or a coating binder. Particular preference is given to polyolefins and polystyrene.

The composition may also comprise a further component selected from solvents, pigments, dyes, plasticizers, antioxidants, thixotropic agents, levelling assistants, further light stabilizers, metal passivators, metal oxides, organophosphorus compounds, hydroxylamines, UV absorbers, sterically hindered amines, and mixtures thereof.

Examples for such further components are given below.
1. Antioxidants
1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1-yl)phenol, 2,4-dimethyl-6-(1-methylheptadec-1'-yl)phenol, 2,4-dimethyl-6-(1'-methyltridec-1-yl)phenol and mixtures thereof.

1.2. Alkylthiomethylphenols, for example 2,4-dioctylthiomethyl-6-tert-butylphenol, 2,4-dioctyl-thiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butyl-phenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxy-benzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, didodecylmercaptoethyl-2,2-bis (3,5-di-tert-butyl-4-hydroxybenzyl)malonate, bis[4-(1,1,3,3-te-tramethylbutyl)phenyl]-2,2-bis(3,5-di-tert-butyl-4-hydroxybenzyl) malonate.

1.9. Aromatic hydroxybenzyl compounds, for example 1,3,5-tris(3,5-di-tert-butyl-4-hydroxy-benzyl)-2,4,6-trimethylbenzene, 1,4-bis(3,5-di-tert-butyl-4-hydroxybenzyl)-2,3,5,6-tetramethyl benzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxy-anilino)-1,3,5-triazine, 2-octylmercapto-4,6-bis(3,5-di-tert-butyl-4-hydroxyanilino)-1,3,5-tri-azine, 2-octylmercapto-4,6-bis(3,5-di-tertbutyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)iso-cyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, tri-ethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxy-phenylpropionyl)trimethylenediamide, N,N'-bis(3,5-di-tert-butyl-4-hydroxyphenylpropionyphydrazide, N,N'-bis[2-(3-[3,5-di-tert-butyl-4-hydroxyphenyl]propionyloxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenyl-amine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butyl-aminophenol, 4-butyrylaminophenol, 4-nonanoylaminophenol, 4-dodecanoylaminophenol, 4-octadecanoylaminophenol, bis (4-methoxyphenyl)amine, 2,6-di-tert-butyl-4-dimethylamino-methylphenol, 2,4'-diaminodiphenylmethane, 4,4'-diaminodiphenylmethane, N,N,N',N'-tetra-methyl-4,4'-diaminodiphenylmethane, 1,2-bis[(2-methylphenyl)amino] ethane, 1,2-bis(phenyl-amino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenyl-amines, a mixture of mono- and dialkylated nonyldiphenylamines, a mixture of mono- and dialkylated dodecyldiphenylamines, a mixture of mono- and dialkylated isopropyl/isohexyl-diphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene.

2. UV absorbers and light stabilizers 2.1. 2-(2'-Hydroxyphenyl)benzotriazoles, for example 2-(2'-hydroxy-5'-methylphenyl)-benzo-triazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-meth-oxycarbonylethyl) phenyl)benzotriazole, 2-(3'-tert-butyl-2'-hydroxy-5'-(2-octyloxycarbonyl-ethyl)phenyl)benzotriazole, 2-(3'-tert-butyl-5'-[2-(2-ethylhexyloxy)carbonylethyl]-2'-hydroxy-phenyl) benzotriazole, 2-(3'-dodecyl-2'-hydroxy-5'-methylphenyl) benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]-benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyl-oxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycin-namate, N-(β-carbomethoxy-β-cyanovinyl)-2-methylindoline, neopentyl tetra(α-cyano-β,β-di-phenylacrylate.

2.5. Nickel compounds, for example nickel complexes of 2,2'-thio-bis[4-(1,1,3,3-tetramethyl-butyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphe-nylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyphexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenypethene, 4-Piperidinol, 2,2,6,6-tetramethyl-1-(undecyloxy)-4,4'-carbonate, N,N'-bis-formyl-N,N'-bis(2,2,6,6-tetramethyl-4-piperidyphexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-a-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethyl-piperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)-oxymethyl-3,3,5-trimethyl-2-morpholinone, Sanduvor (Clariant; CAS Reg. No. 106917-31-1], 5-(2-ethylhexanoyl)oxymethyl-3,3,5-trimethyl-2-morpholinone, the reaction product of 2,4-bis-[(1-cyclohexyloxy-2,2,6,6-piperidine-4-yl)butylamino]-6-chloro-s-triazine with N,N'-bis (3-aminopropyl)ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)-amino)-s-triazine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-1-hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy) phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxy-phenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl)phosphite, trilauryl phosphite, trioctadecyl phosphite, distearylpentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,4-dicumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)-pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo-[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:

Tris(2,4-di-tert-butylphenyl) phosphite (Irgafos 168, Ciba Specialty Chemicals Inc.), tris(nonylphenyl)phosphite,

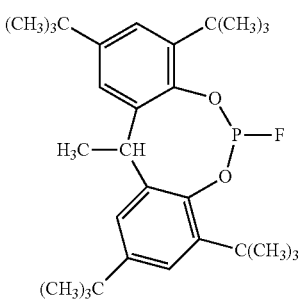
(A)

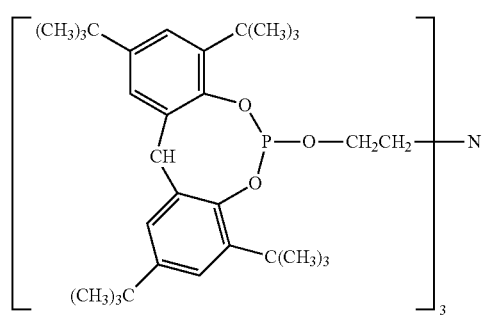
(B)

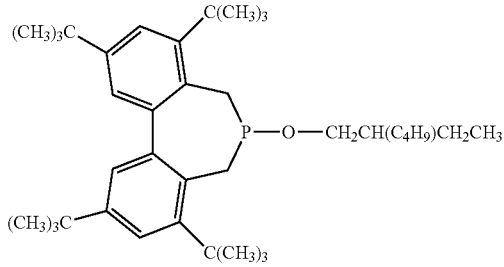
(C)

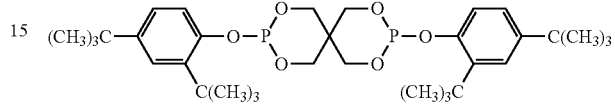
(D)

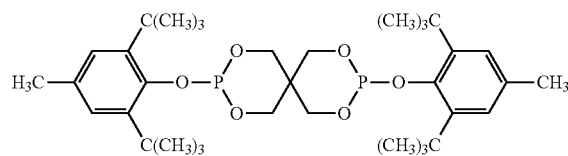
(E)

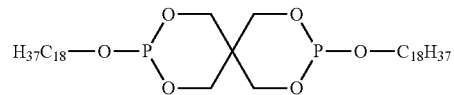
(F)

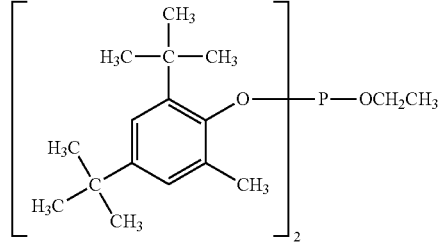
(G)

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-hepta-decylnitrone, N-octadecyl-alpha-hexadecylnitrone, nitrone derived from N,N-dialkylhydroxyl-amine derived from hydrogenated tallow amine.

7. Thiosvnergists, for example dilauryl thiodipropionate, dimistryl thiodipropionate, distearyl thiodipropionate or distearyl disulfide.

8. Peroxide scavengers, for example esters of P-thiodipropionic acid, for example the lauryl, stearyl, myristyl or tridecyl esters, mercaptobenzimidazole or the zinc salt of 2-mercapto-benzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyl-dibenzylidene)sorbitol, and 1,3:2,4-di(benzylidene)sorbitol.

12. Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839, EP-A-0591102; EP-A-1291384 or 3-[4-(2-acetoxyethoxy)phenyl]-5,7-di-tert-butylbenzofuran-2-one, 5,7-di-tert-butyl-3-[4-(2-stearoyloxy-ethoxy)phenyl]benzofuran-2-one, 3,3'-bis[5,7-di-tert-butyl-3-(4-[2-hydroxyethoxy]phenyl)ben-zofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one, 3-(2-acetyl-5-isooctylphenyl)-5-isooctyl-benzofuran-2-one.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized compositions of the invention may optionally also contain from about 0.01 to about 5%, preferably from about 0.025 to about 2%, and especially from about 0.1 to about 1% by weight, based on the weight of the polymer of various conventional additives, such as the materials listed above, or mixtures thereof.

Yet further aspects of the invention are a process for stabilizing an organic polymeric material against damage by light, oxygen and/or heat, which comprises adding to or applying to said material at least one compound according to formula (I) or (II) or of formulae Id), (Id'), (Ie), (Ie'), (If), (If'), (IIa) or (IIb) as described above; and the use of a compound according to formula (I) or (II) or of formulae Id), (Id'), (Ie), (Ie'), (If), (If'), (IIa) or (IIb) as described above for stabilizing an organic polymer against damage by light, oxygen and/or heat or as flame retardant.

Also an aspect of the invention are the intermediate compounds of formulae 1, 2 or 3

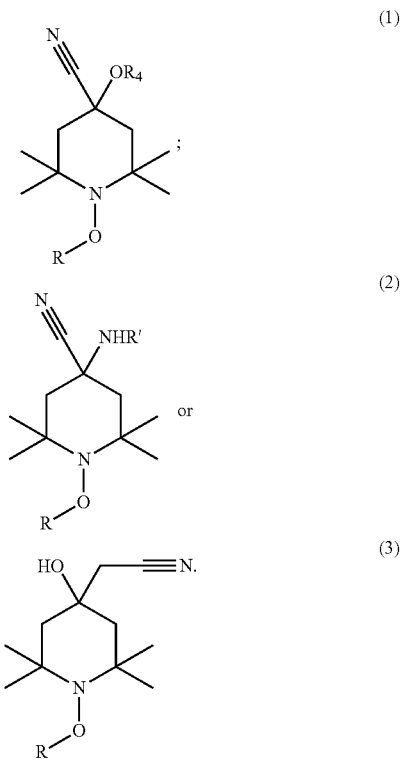

wherein $R_4$ is H or $Si(CH_3)_3$ and R and R' have the meaning as defined above; with the proviso that in formula (2) R' is not H.

Definitions and preferences given above apply equally for all aspects of the invention.

The following examples illustrate the invention.

PREPARATION EXAMPLES

4-Oxo-N-alkoxyamines are prepared according to WO 2008003602

Example 1

Preparation of 1-Methoxy-4-cyano-4-hydroxy-2,2,6,6-tetramethyl-1-piperidine

To a mixture of 2.5 g 1-methoxy-2,2,6,6-tetramethyl-piperidin-4-one, 1 equivalent sodium cyanide and 10 ml water is added at 5-10° C. a solution of 0.73 g conc. sulfuric acid in 3.2 ml water over a period of 2-3 h. Stirring is continued for another 45 min. whereupon the solid material is separated by filtration. The filter cake is washed with cold water and dried in vacuo at room temperature. The product is obtained as colorless crystals, 1.7 g. $^1$H-NMR (CDCl$_3$, 300 MHz): δ 3.55 (s, 3H), 2.48 (d, 1H), 2.03 (d, 1H), 1.99 (s, 1H), 1.76 (d, 1H), 1.31 (s, 3H), 1.25 (s, 3H), 1.22 (s, 3H), 1.16 (s, 3H). MS: m/z=212.9 [M+H]$^+$.

Example 2a

Preparation of 1-Methoxy-2,2,6,6-tetramethyl-4-cyano-4-trimethylsilyloxy-piperidine To a soln. of 3.26 g 1-methoxy-2,2,6,6-tetramethyl-piperidin-4-one in 40 ml of dichloro-methane is added 2.09 g trimethylsilyl cyanide and 0.28 g tetrabutylammonium phthalimide-N-oxyl (TBAPINO, prepared according to Dekamin et al, Catalysis communications 2009, 582). After 2 h of stirring at rt, the ketone is completely converted. The reaction mixture is diluted with 90 ml ethyl acetate and 20 ml hexane. After washing with water and drying over sodium sulfate, the organic solvents are removed in vacuo to afford 4.7 g of 1-methoxy-2,2,6,6-tetramethyl-4-cyano-4-trimethylsilyloxypiperidine (yellow oil).

$^1$H-NMR (CDCl$_3$, 300 MHz): δ 3.63 (s, 3H), 2.27-1.79 (m, 4H), 1.39 (s, 3H), 1.31 (s, 3H), 1.29 (s, 3H), 1.27 (s, 3H), 0.28 (s, 9H). MS: m/z=285 [M+H]$^+$.

Example 2b

Preparation of 1-Ethoxy-2,2,6,6-tetramethyl-4-cyano-4-trimethylsilyloxy-piperidine To a solution of 0.398 g (2 mmol) 1-ethoxy-2,2,6,6-tetramethyl-piperidin-4-one in dry acetonitrile is added 0.297 g (3 mmol) trimethylsilyl cyanide and a catalytic amount of iodine. The solution is stirred at rt over night. The reaction mixture is extracted with ethyl acetate, washed with Na$_2$CO$_3$ solution and brine. The organic layer is separated, dried over Na$_2$SO$_4$, filtered and the solvent is removed under reduced pressure. A yellow oil was obtained and subsequently subjected to flash chromatography on silica gel using 4:1 hexane/ethyl acetate as eluent. The product was obtained as a pale yellow oil.

$^1$H-NMR (CDCl$_3$) δ: 3.78 (q, 2H); 2.14 (m, 1H); 2.00 (m, 2H); 1.80 (m, 1H); 1.39 (s, 3H); 1.31 (s, 3H); 1.21 (s, 3H); 1.19 (s, 3H); 1.12 (t, 3H); 0.27 (s, 6H); 0.25 (s, 3H). $^{13}$C-NMR (CDCl$_3$) δ: 121.0; 71.5; 66.5; 64.1; 58.0; 57.7; 49.4; 48.3; 32.6; 20.1; 19.7; 12.5; 0.6. MS: m/z=299 [M+H]$^+$.

Example 3

8-Methoxy-2,2,7,7,9,9-hexamethyl-3-oxiranylmethyl-1-oxa-3,8-diaza-spiro[4.5]decan-4-one 1.0 g of 1-methoxy-2,2,6,6-tetramethyl-4-cyano-4-trimethylsilyloxypiperidine is dissolved in 1.76 g acetic acid and 0.48 g acetone is added. 0.7 g conc. sulfuric acid is added and the reaction mixture is stirred at 70° C. for 18 h while forming a deep red solution. The reaction mixture is added to 40 ml saturated NaHCO$_3$ solution, and extracted with 40 ml ethyl acetate. The organic phase is washed with H$_2$O and subsequently dried over sodium sulfate. The solvent is removed in vacuo to leave 0.87 g of a tan residue. After washing the residue with n-hexane, 8-methoxy-2,2,7,7,9,9-hexamethyl-1-oxa-3,8-diaza-spiro[4.5]decan-4-one is obtained as a white solid (0.46 g), mp. 230° C.

$^1$H-NMR (CDCl$_3$, 300 MHz): δ 3.55 (s, 3H), 1.93 (dd, 2H), 1.55 (dd, 2H), 1.41 (s, 6H), 1.25 (s, 6H), 1.13 (s, 6H). C13-NMR (CDCl$_3$, 75 MHz): δ 176.4, 89.4, 80.8, 65.6, 58.8, 46.4, 33.5, 30.4, 20.6. MS: m/z=271.0 [M+H]$^+$.

Example 4

Alternative Method for the Preparation of 8-Methoxy-2,2,7,7,9,9-hexamethyl-3-oxiranylmethyl-1-oxa-3,8-diaza-spiro[4.5]decan-4-one 1.0 g of 1-methoxy-2,2,6,6-tetramethyl-4-cyano-4-hydroxypiperidine is dissolved in 2.0 g acetic acid and 0.65 g acetone is added. 0.8 g conc. sulfuric acid is added and the reaction mixture is stirred at 70° C. for 18 h. The reaction mixture is added to 40 ml saturated NaHCO$_3$ solution, and extracted with ethyl acetate. The organic phase is washed with H$_2$O and subsequently dried over sodium sulfate. The solvent is removed in vacuo to leave 0.71 g of a tan residue. After washing the residue with n-hexane, 8-methoxy-2,2,7,7,9,9-hexamethyl-1-oxa-3,8-diaza-spiro[4.5]decan-4-one is obtained as a white solid.

$^1$H-NMR (CDCl$_3$, 300 MHz): δ 3.56 (s, 3H), 1.93 (dd, 2H), 1.55 (dd, 2H), 1.41 (s, 6H), 1.25 (s, 6H), 1.13 (s, 6H). C13-NMR (CDCl$_3$, 75 MHz): δ 176.4, 89.4, 80.8, 65.6, 58.8, 46.4, 33.5, 30.4, 20.6. MS: m/z=271 [M+H]$^+$.

Examples 5-9

Using the Product of Example 2 as Starting Material, the following Examples were Prepared in Analogy to Examples 3, 4

| Example | Carbonyl compound | product | MS data |
|---|---|---|---|
| 5 | butanone | 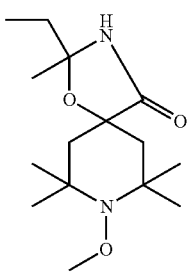 [SMILES: CCC1(C)NC(=O)C2(CC(C)(C)N(OC)C(C)(C)C2)O1] | MS: m/z = 285 [M + H]$^+$. |

-continued

| Example | Carbonyl compound | product | MS data |
|---|---|---|---|
| 6 | cyclohexanone | | MS: m/z = 311 [M + H]⁺. |
| 7a | Dodecanone | | MS: m/z = 395 [M + H]⁺. |
| 7b | | | |
| 7c | | | |
| 8 | | | MS: m/z = 398 [M + H]⁺. |

| Example | Carbonyl compound | product | MS data |
|---|---|---|---|
| 9 | Butanal | | MS: m/z = 285 [M + H]+. |

Example 10

8-Methoxy-7,7,9,9-tetramethyl-1,3,8-triaza-spiro[4.5]decane-2,4-dione

A mixture of 1.0 g 1-Methoxy-2,2,6,6-tetramethyl-piperidin-4-one, 527 mg potassium cyanide and 3.11 g ammonium carbonate in 21 ml water/ethanol (2:1) is stirred at 50° C. After several hours of stirring a white precipitate forms. Stirring is continued for 24 h, whereupon the precipitate is isolated by filtration. The filter cake is washed with water and ethanol and dried in vacuo. The product is obtained as a white solid, 0.99 g.
$^1$H-NMR (CDCl$_3$, 300 MHz): δ 10.78 (br s, 1H), 3.56 (s, 3H), 1.87 (dd, 2H), 1.58 (dd, 2H), 1.19 (2s, 6H), 1.13 (2s, 6H). C$^{13}$-NMR (CDCl$_3$, 75 MHz): δ 178.3, 156.5, 65.11, 60.5, 57.5, 45.6, 33.4, 20.2. MS: m/z=256 [M+H]+.

Example 11

8-Methoxy-7,7,9,9-tetramethyl-1-oxa-3,8-diaza-spiro[4.5]decan-4-one 0.61 g of 1-Methoxy-2,2,6,6-tetramethyl-piperidin-4-one and 299 mg acetone cyanhydrine are dissolved in 1.76 g acetic acid and 0.7 g conc. sulfuric acid is added. The reaction mixture is stirred at 70° C. for 18 h. The reaction mixture is added to 40 ml saturated NaHCO$_3$ solution, and extracted with 40 ml ethyl acetate. The organic phase is washed with H$_2$O and subsequently dried over sodium sulfate. The solvent is removed in vacuo to leave 0.61 g of a tan residue. The residue is recrystallized from hexane to yield 0.29 g product. White solid, mp. 130° C.
$^1$H-NMR (CDCl$_3$, 300 MHz): δ 7.04 (br s, 1H), 3.54 (s, 3H), 1.71 (2 d, 4H), 1.33 (s, 6H), 1.25 (s, 6H), 1.12 (s, 6H). C$^{13}$-NMR (CDCl$_3$, 75 MHz): δ 177.3, 88.9, 79.9, 65.5, 59.6, 50.8, 33.5, 26.4, 20.6. MS: m/z=271.0 [M+H]+.

Example 12

(1-Ethoxy-4-hydroxy-2,2,6,6-tetramethyl-piperidin-4-yl)-acetonitrile 3 g 1-Ethoxy-2,2,6,6-tetramethyl-piperidin-4-one is dissolved in 20 ml dry THF and 0.93 g acetonitrile are added. The mixture is cooled to −78° C. and 9.4 ml n-butyllithium (1.6 M solution in hexane) are added over a period of 30 min. Stirring is continued at −78° C. for 1 h, then the cooling bath is removed. After 2 h stirring at room temperature, the reaction mixture is diluted with MTBE and quenched with ammonium chloride solution. The organic phase is washed with water and brine, dried over sodium sulfate, and the solvent is removed in vacuo. The residue obtained is recrystallized from toluene to obtain the product as colorless crystals. $^1$H-NMR (CDCl$_3$, 300 MHz): δ 3.78 (q, 2H), 2.43 (s, 2H), 1.93 (s, OH), 1.81 (2 d, 4H), 1.68 (d, 2H), 1.37 (s, 6H), 1.16 (s, 6H), 1.13 (t, 3H). C$^{13}$-NMR (CDCl$_3$, 75 MHz): δ 117.3, 72.5, 70.0, 58.8, 48.3, 34.8, 33.9, 21.1, 13.2. MS: m/z=241.0 [M+H]+.

APPLICATION EXAMPLES

Polypropylene (Moplen® HF500 N) is extruded on a co-rotating twin-screw extruder ZSK18 (Coperion Werner & Pfleiderer) at a temperature of Tmax=190° C. (heating zones 1-7), a throughput rate of 1 kg/h and 100 rpm with the addition of a basic-level stabilization (0.3% IRGANOX B225+0.05% Ca-stearate, IRGANOX B225 is a 1:1 mixture of IRGAFOS 168 and IRGANOX 1010) and 0.5 weight % of each of the compounds of example 7, 11, 10b and 10c. After cooling in a water bath, the polymer strand is granulated. Test specimens are prepared by compression moulding (films 190×90 mm, thickness=0.2 mm or 1.0 mm, Fontune TP200, 230° C.). Test films are tested under DIN 4102-1 B2 test conditions. The results are presented in Table B1 and Table B2.

TABLE B1

| Compound | Burning time [s] | Damaged length [mm] |
|---|---|---|
| Blank | 36.3 | 190 |
| Compound of example 10 | 9.7 | 72 |

DIN 4102 - B2 (Edge Ignition, Flame length 40 mm, Distance 16 mm). PP Film Thickness 200 microns; Length: 190 mm; Width: 90 mm; Conditioning Procedure: 3 days 50%/23° C. in conditioning chamber; Lab. humidity 50%/Temp: 23° C.

TABLE B2

| Compound (0.5%) | Damaged length [mm] | Burning time [s]; 0.2 mm | Damaged length 1.0 mm [mm] | Burning time [s]; 1.0 mm |
| --- | --- | --- | --- | --- |
| Blank | 190 | 41.3 | 190 | 137.3 |
| Compound of example 7a | 71 | 8.3 | 75 | 47.5 |
| Compound of example 7b | 76 | 12 | — | — |
| Compound of example 7c | 66 | 13.7 | 74 | 45.3 |
| | DIN 4102-B2 (Edge Ignition, Flame length 40 mm, Distance 16 mm). PP Film Thickness 200 microns; Length: 190 mm; Width: 90 mm; Conditioning Procedure: 3 days 50%/23° C. in conditioning chamber; Lab. humidity 50%/ Temp: 23° C. | | DIN 4102-B2 (Edge Ignition, Flame length 40 mm, Distance 16 mm). PP Film Thickness 1.0 mm; Length: 190 mm; Width: 90 mm; Conditioning Procedure: 3 days 50%/23° C. in conditioning chamber; Lab. humidity 50%/Temp: 23° C. | |

The invention claimed is:
1. A process for preparing a compound of formula (I), (II), (Id), (Id'), (Ie), (Ie'), (If), (If'), (IIa) or (IIb)
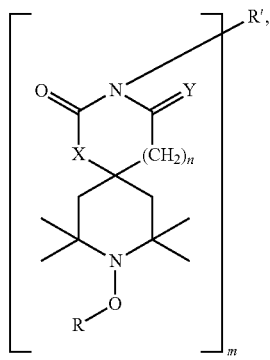
(I)
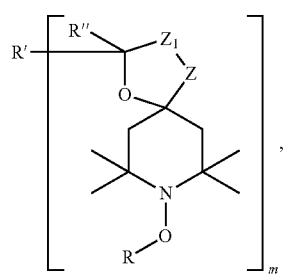
(II)
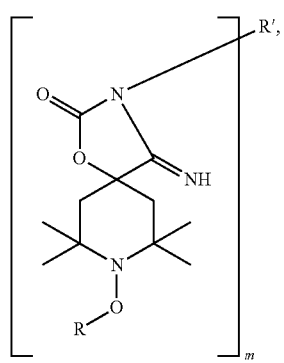
(Id)
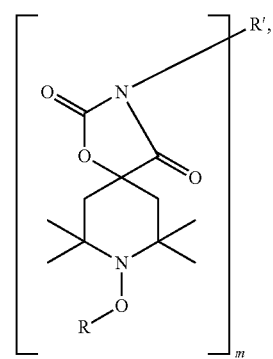
(Id')
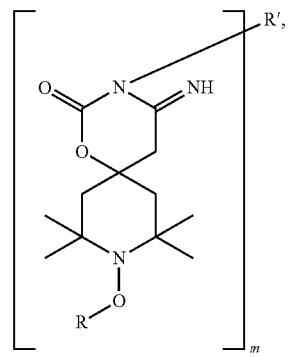
(Ie)
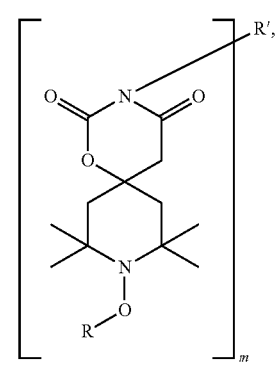
(Ie')
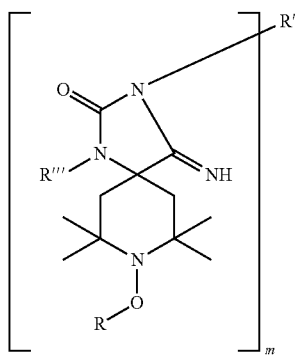
(If)
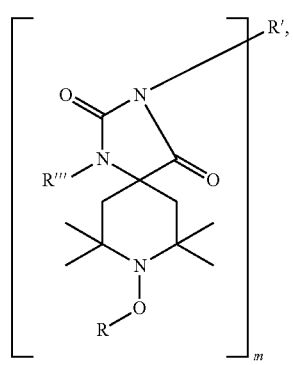
(If')

-continued

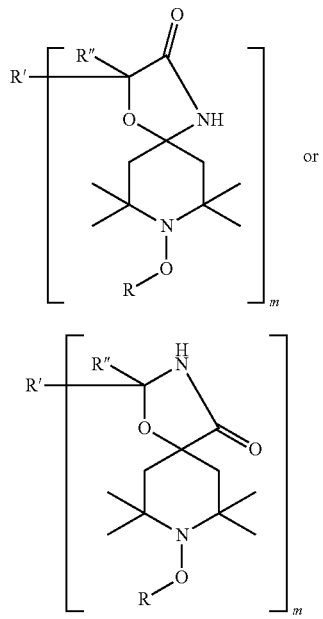

(IIa)

or (IIb)

wherein

X and Y are independently NH or O;

m is 1 or 2;

n is 1;

Z is C=O and $Z_1$ is NH; or

Z is NH and $Z_1$ is C=O;

R is $C_1$-$C_{20}$alkyl, $C_3$-$C_{20}$alkenyl, $C_3$-$C_{20}$alkynyl which are unsubstituted or substituted by OH, halogen, $NO_2$, carbonyl or carboxyl; phenyl, $C_7$-$C_{12}$phenylalkyl or $C_3$-$C_{12}$cycloalkyl;

if m is 1

R' and R" are independently H, $C_1$-$C_{20}$alkyl, $C_3$-$C_{20}$alkenyl, $C_3$-$C_{20}$alkynyl which are unsubstituted or substituted by OH, halogen, $NO_2$, carbonyl or carboxyl; phenyl, $C_7$-$C_{12}$phenylalkyl or $C_3$-$C_{12}$cycloalkyl;

with the proviso that if in formula (II) Z is C=O, R is not octyl or methylbenzyl;

if m is 2

R" is H, $C_1$-$C_{20}$alkyl, $C_3$-$C_{20}$alkenyl, $C_3$-$C_{20}$alkynyl which are unsubstituted or substituted by OH, halogen, $NO_2$, carbonyl or carboxyl; phenyl, $C_7$-$C_{12}$phenylalkyl or $C_3$-$C_{12}$cycloalkyl; and R' $C_1$-$C_{20}$ alkylene, $C_5$-$C_{12}$cycloalkylene, phenylene, $C_1$-$C_4$alkylene-$C_5$-$C_{12}$cycloalkylene-$C_1$-$C_4$alkylene, $C_1$-$C_4$alkylene-phenylene-$C_1$-$C_4$alkylene wherein the phenylene and the $C_5$-$C_{12}$cycloalkyne radicals are unsubstituted or substituted by 1 to 4 $C_1$-$C_4$alkyl groups;

R''' is H, $C_1$-$C_{20}$alkyl, $C_3$-$C_{12}$cycloalkyl, phenyl or $C_7$-$C_{12}$phenylalkyl;

and if m is 1 with the proviso that in formula (IIb), R is not octyl or methylbenzyl; and in formula (If'), R' is not H when R''' is H, comprising at least one reaction selected from the group consisting of:

a) reacting a compound of formula (O)

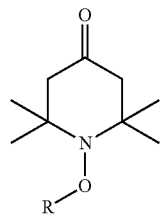

(O)

with HCN or a precursor of HCN or with a compound of formula

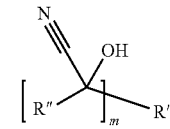

to obtain a compound of formula (1)

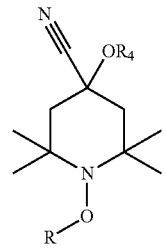

(1)

wherein $R_4$ is H or Si(CH$_3$)$_3$; and b) reacting a compound of formula (1) with an amine of formula R'''—NH$_2$ to yield a compound of formula (2)

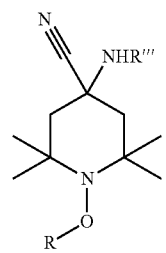

(2)

where R''' is H, $C_1$-$C_{20}$alkyl, $C_3$-$C_{12}$cycloalkyl, phenyl or $C_7$-$C_{12}$phenylalkyl or reacting a compound of formula (O) with HCN or a precursor of HCN in the presence of an amine or ammonia; or c) reacting a compound of formula (O) with CH$_3$CN and a base to obtain a compound of formula (3)

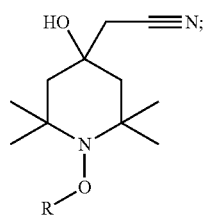
(3)

or
d) reacting a compound of formula (O) with a compound of formula

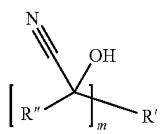

to obtain a compound of formula (IIa); and in a further step
e) reacting the compound of formula (1) with an aldehyde, dialdehyde, ketone, or diketone of formula

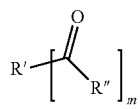

to obtain a compound of formula (IIb) or
reacting the compound of formula (1) with an isocyanate or diisocyanate of formula R'—[NCO]$_m$ to obtain a compound of formula (Id), (Id'); or
f) reacting a compound of formula (2) with an isocyanate of formula R'—[NCO]$_m$ to obtain a compound of formula (If), (If'); and or
g) reacting a compound of formula (3) with an isocyanate of formula R'—[NCO]$_m$ to obtain a compound of formula (Ie), (Ie')
wherein a pressure of said process is from atmospheric pressure to 100 bar.

2. The process of claim 1, wherein a temperature of the process is from −20° C. to 100° C.

3. A compound of formulae 1, 2, or 3

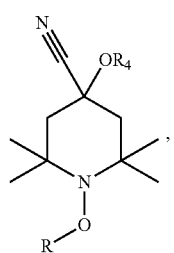
(1)

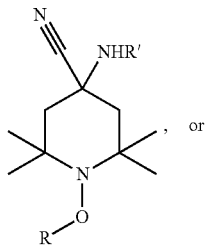
(2)

, or

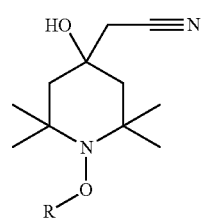
(3)

wherein R$_4$ is Si(CH$_3$)$_3$;
R is C$_1$-C$_{20}$alkyl; C$_3$-C$_{20}$alkenyl; C$_3$-C$_{20}$alkynyl optionally substituted by OH, halogen, NO$_2$, carbonyl or carboxyl; phenyl; C$_7$-C$_{12}$phenylalkyl; or C$_3$-C$_{12}$cycloalkyl; and
R' is C$_2$-C$_{20}$alkyl; C$_3$-C$_{20}$alkenyl; C$_3$-C$_{20}$alkynyl optionally substituted by OH, halogen, NO$_2$, or carboxyl; phenyl; C$_7$-C$_{12}$phenylalkyl; C$_3$-C$_{12}$cycloalkyl.

4. A compound of formula (I) or (II)

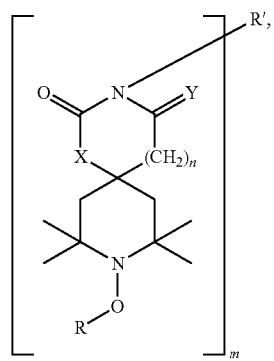
(I)

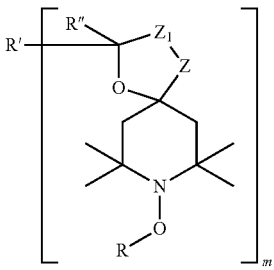
(II)

wherein
X and Y are independently NH or O;
m in formula (I) is 1 or 2;
m in formula (II) is 2;
n is 1;
Z is C=O and Z$_1$ is NH; or
Z is NH and Z$_1$ is C=O;

R is $C_1$-$C_{20}$alkyl, $C_3$-$C_{20}$alkenyl, $C_3$-$C_{20}$alkynyl which are unsubstituted or substituted by OH, halogen, $NO_2$, carbonyl or carboxyl; phenyl, $C_7$-$C_{12}$phenylalkyl or $C_3$-$C_{12}$cycloalkyl;

if m is 1

R' and R" are independently H, $C_1$-$C_{20}$alkyl, $C_3$-$C_{20}$alkenyl, $C_3$-$C_{20}$alkynyl which are unsubstituted or substituted by OH, halogen, $NO_2$, carbonyl or carboxyl; phenyl, $C_7$-$C_{12}$phenylalkyl or $C_3$-$C_{12}$cycloalkyl;

with the proviso that if in formula (II) Z is C=O, R is not octyl or methylbenzyl;

if m is 2

R" is H, $C_1$-$C_{20}$alkyl, $C_3$-$C_{20}$alkenyl, $C_3$-$C_{20}$alkynyl which are unsubstituted or substituted by OH, halogen, $NO_2$, carbonyl or carboxyl; phenyl, $C_7$-$C_{12}$phenylalkyl or $C_3$-$C_{12}$cycloalkyl; and R' $C_1$-$C_{20}$ alkylene, $C_5$-$C_{12}$cycloalkylene, phenylene, $C_1$-$C_4$alkylene-$C_5$-$C_{12}$cycloalkylene-$C_1$-$C_4$alkylene, $C_1$-$C_4$alkylene-phenylene-$C_1$-$C_4$alkylene wherein the phenylene and the $C_5$-$C_{12}$cycloalkyne radicals are unsubstituted or substituted by 1 to 4 $C_1$-$C_4$alkyl groups.

5. A compound of formula (Id), (Id'), (Ie) or (Ie')

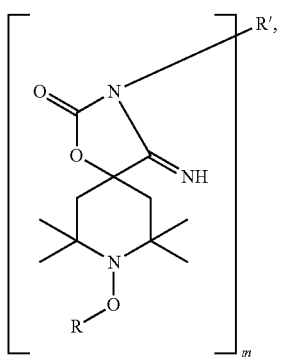
(Id)

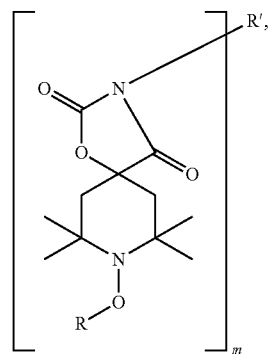
(Id')

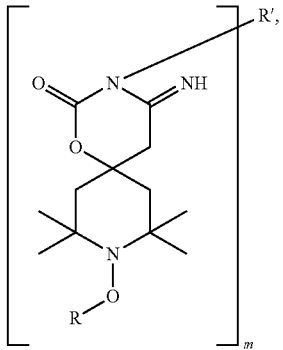
(Ie)

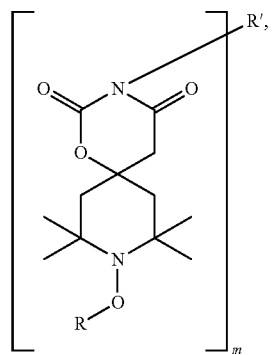
(Ie')

wherein m is 1 or 2;

R is $C_1$-$C_{20}$alkyl, $C_3$-$C_{20}$alkenyl, $C_3$-$C_{20}$alkynyl which are unsubstituted or substituted by OH, halogen, $NO_2$, carbonyl or carboxyl; phenyl, $C_7$-$C_{12}$phenylalkyl or $C_3$-$C_{12}$cycloalkyl;

if m is 1

R' and R" are independently H, $C_1$-$C_{20}$alkyl, $C_3$-$C_{20}$alkenyl, $C_3$-$C_{20}$alkynyl which are unsubstituted or substituted by OH, halogen, $NO_2$, carbonyl or carboxyl; phenyl, $C_7$-$C_{12}$phenylalkyl or $C_3$-$C_{12}$cycloalkyl;

if m is 2

R" is H, $C_1$-$C_{20}$alkyl, $C_3$-$C_{20}$alkenyl, $C_3$-$C_{20}$alkynyl which are unsubstituted or substituted by OH, halogen, $NO_2$, carbonyl or carboxyl; phenyl, $C_7$-$C_{12}$phenylalkyl or $C_3$-$C_{12}$cycloalkyl; and R' $C_1$-$C_{20}$ alkylene, $C_5$-$C_{12}$cycloalkylene, phenylene, $C_1$-$C_4$alkylene-$C_5$-$C_{12}$cycloalkylene-$C_1$-$C_4$alkylene, $C_1$-$C_4$alkylene-phenylene-$C_1$-$C_4$alkylene wherein the phenylene and the $C_5$-$C_{12}$cycloalkyne radicals are unsubstituted or substituted by 1 to 4 $C_1$-$C_4$alkyl groups.

6. A compound according to claims 4 or 5 wherein R is $C_1$-$C_{20}$alkyl, $C_3$-$C_{20}$alkenyl, $C_3$-$C_{20}$alkynyl which are unsubstituted or substituted by OH, carbonyl or carboxyl; phenyl, $C_7$-$C_9$phenylalkyl or $C_5$-$C_8$cycloalkyl;

if m is 1

R' is H, $C_1$-$C_{20}$alkyl, $C_3$-$C_{20}$alkenyl, $C_3$-$C_{20}$alkynyl which are unsubstituted or substituted by OH, carbonyl or carboxyl; phenyl, $C_7$-$C_9$phenylalkyl or $C_5$-$C_8$cycloalkyl;

if m is 2

R' $C_1$-$C_{20}$ alkylene, $C_5$-$C_{12}$cyclo alkylene, phenylene, $C_1$-$C_4$alkylene-$C_5$-$C_{12}$cycloalkylene-$C_1$-$C_4$alkylene, $C_1$-$C_4$alkylene-phenylene-$C_1$-$C_4$alkylene wherein the phenylene and the $C_5$-$C_{12}$cycloalkyne radicals are unsubstituted or substituted by 1 to 4 $C_1$-$C_4$alkyl groups; and R" is H, $C_1$-$C_{20}$alkyl, $C_3$-$C_{20}$alkenyl, $C_3$-$C_{20}$alkynyl which are unsubstituted or substituted by OH, carbonyl or carboxyl; phenyl, $C_7$-$C_9$phenylalkyl or $C_5$-$C_8$cycloalkyl.

7. A compound according to claim 6 wherein

R is $C_1$-$C_{20}$alkyl, phenyl, $C_7$-$C_9$phenylalkyl or $C_5$-$C_6$cycloalkyl;

if m is 1

R' is H, $C_1$-$C_{20}$alkyl, phenyl, $C_7$-$C_9$phenylalkyl or $C_5$-$C_6$cycloalkyl;

if m is 2

R' C$_1$-C$_{20}$ alkylene, C$_5$-C$_{12}$cycloalkylene, phenylene, C$_1$-C$_4$alkylene-C$_5$-C$_{12}$cycloalkylene-C$_1$-C$_4$alkylene, C$_1$-C$_4$alkylene-phenylene-C$_1$-C$_4$alkylene wherein the phenylene and the C$_5$-C$_{12}$cycloalkyne radicals are unsubstituted or substituted by 1 to 4 C$_1$-C$_4$alkyl groups;

R" is H, C$_1$-C$_{20}$alkyl, phenyl, C$_7$-C$_9$phenylalkyl or C$_5$-C$_6$cycloalkyl.

8. A compound according to claim 4 wherein m is 1.

9. At least one compound selected from the group consisting of:

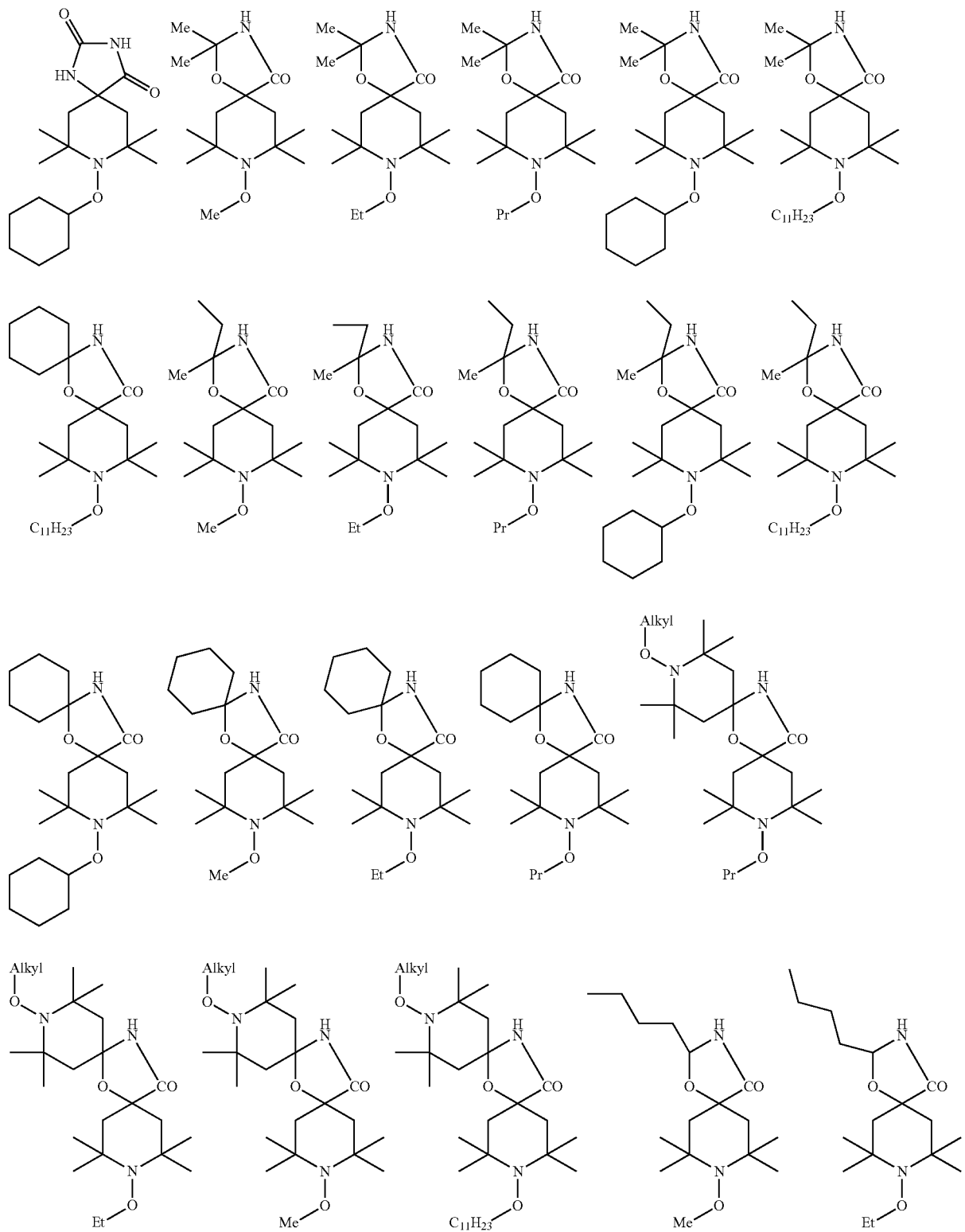

-continued
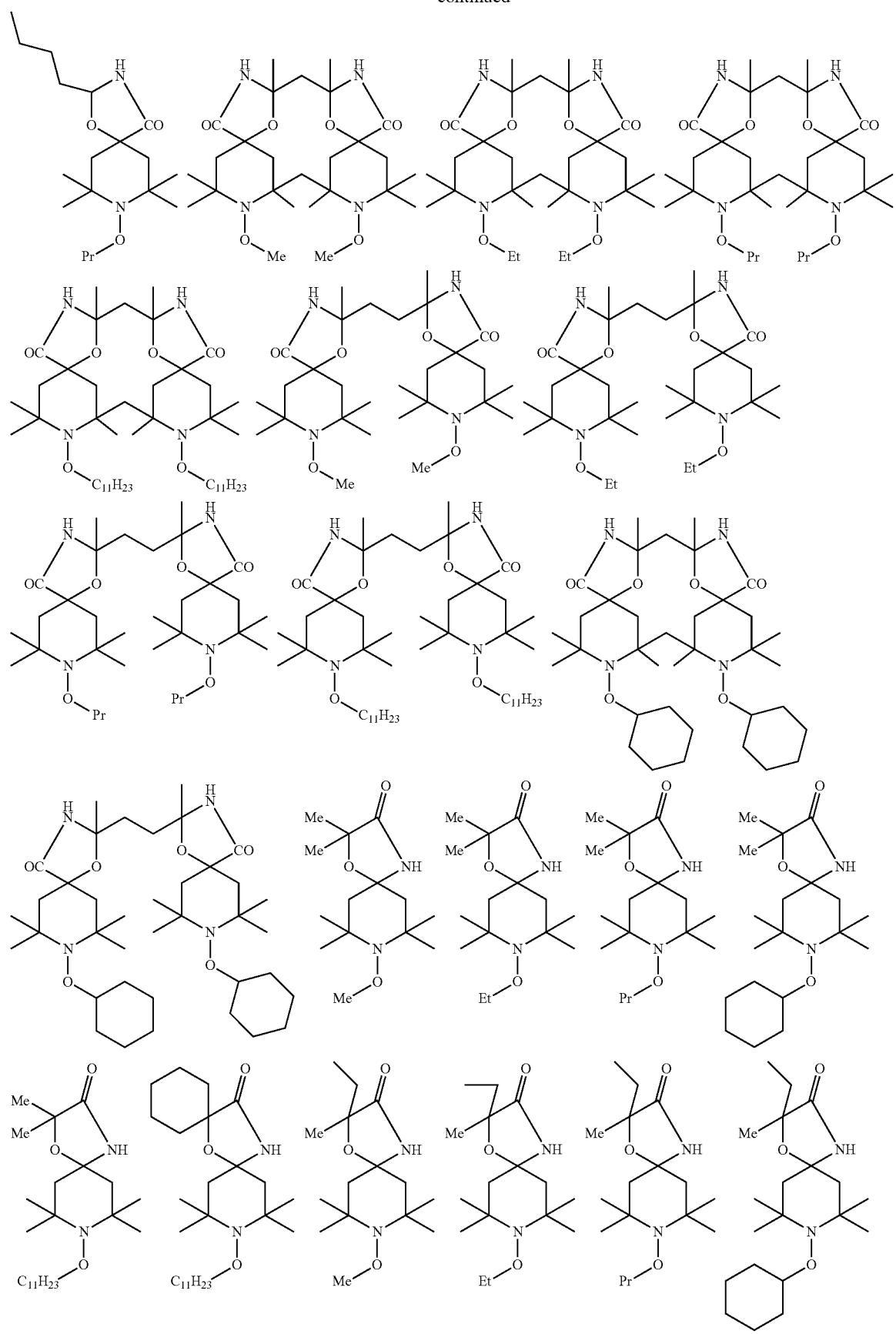

-continued
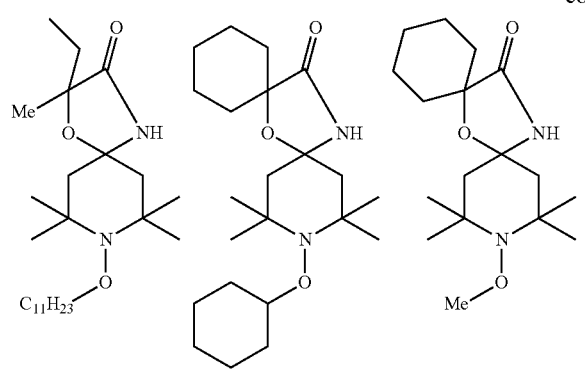
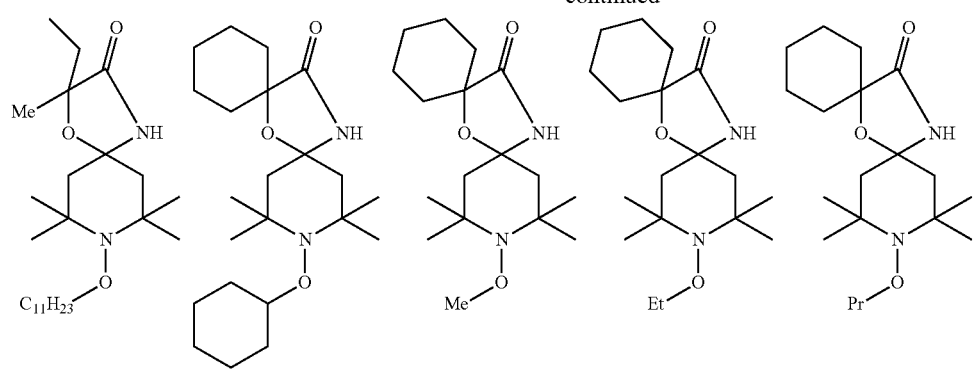
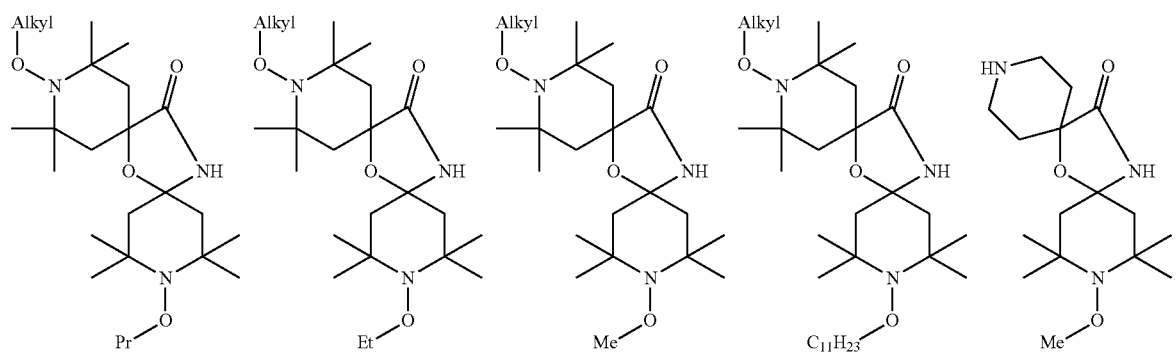
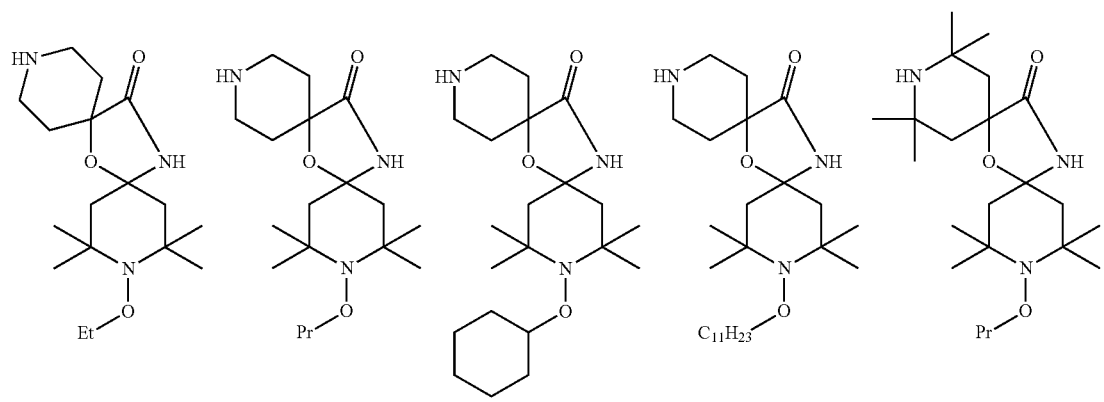
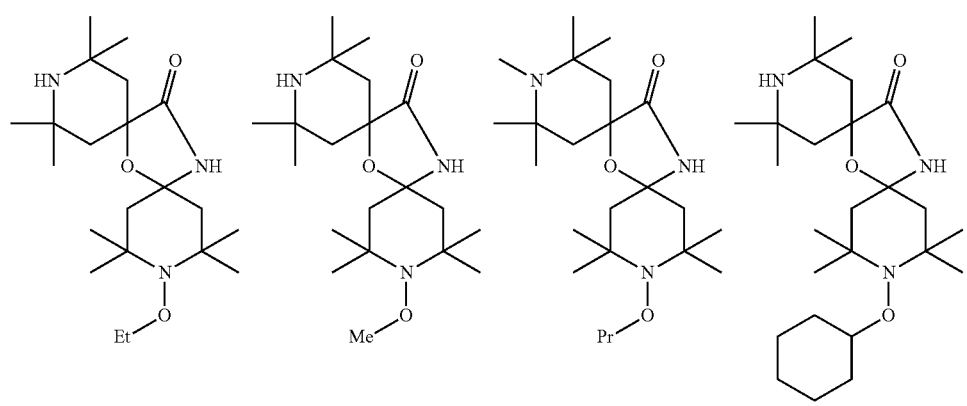

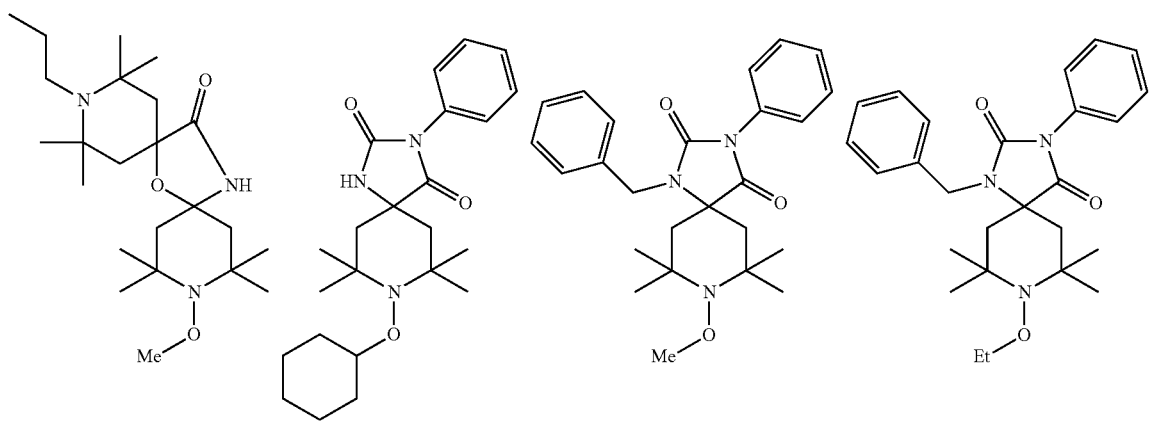
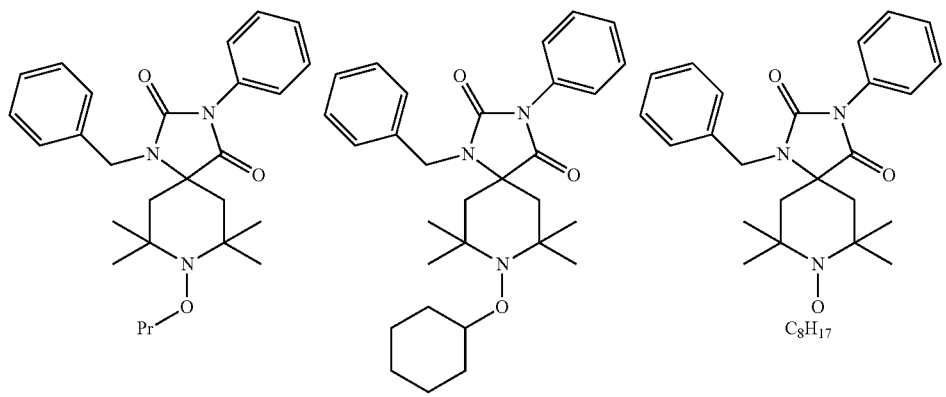
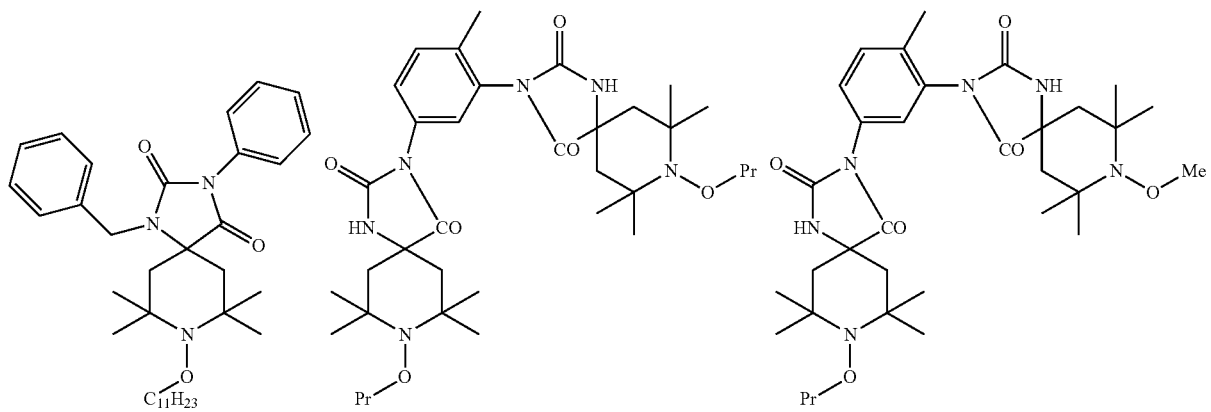
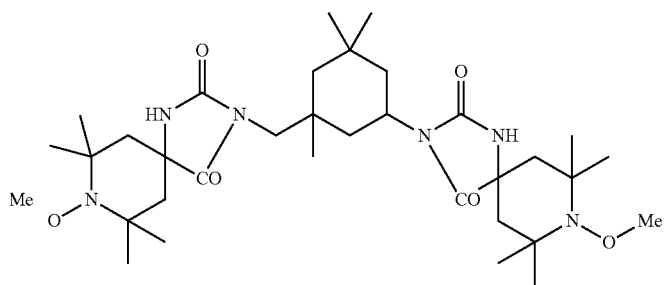

-continued

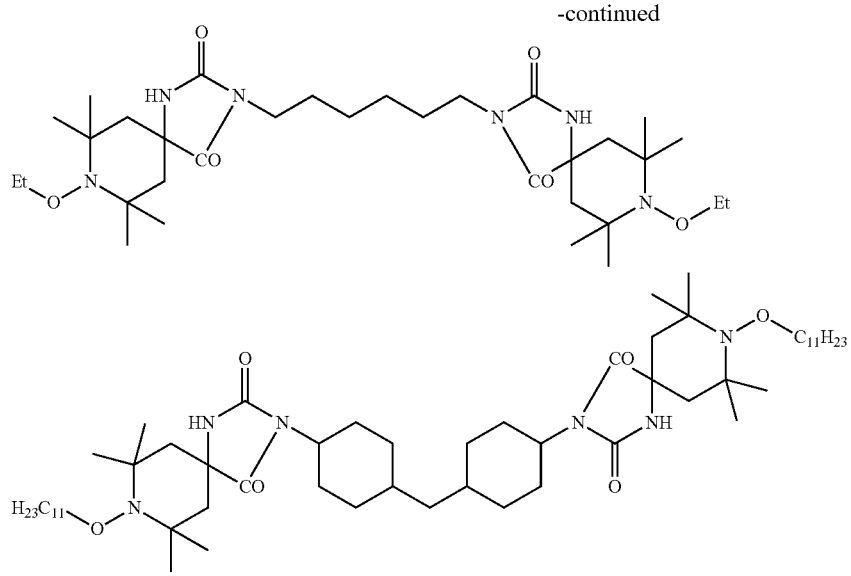

wherein alkyl is a $C_{1-20}$ alkyl group.

10. At least one compound selected from the group consisting of 8-Methoxy-2,2,7,7,9,9-hexamethyl-3-oxiranylmethyl-1-oxa-3,8-diaza-spiro[4.5]decan-4-one, and the compounds of formula

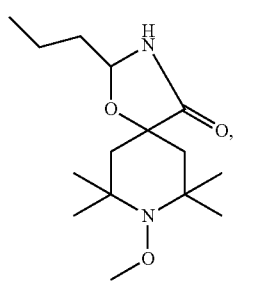 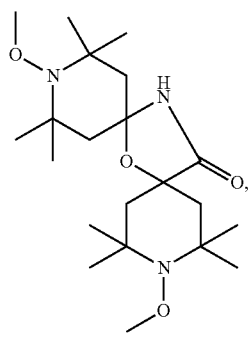

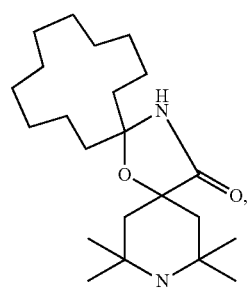

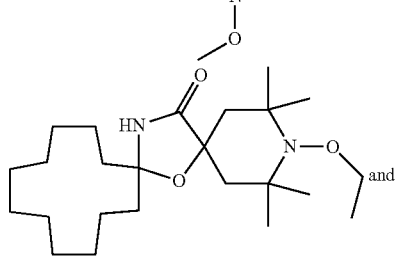
and

-continued

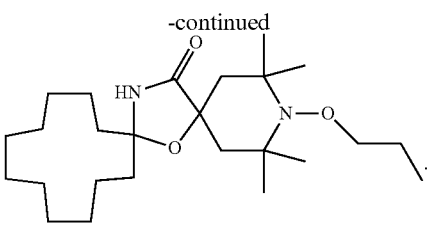

.

11. A composition, comprising:
(a) an organic polymer subject to the adverse effects of heat, oxygen and light, and
(b) the compound of claim 4.

12. The composition of claim 11, wherein the organic polymer is a thermoplastic organic polymer or a coating binder.

13. The composition of claim 11, comprising:
a solvent, a pigment, a dye, a plasticizer, an antioxidant, a thixotropic agent, a levelling assistant, a further light stabilizer, a metal passivator, a metal oxide, an organophosphorus compound, a hydroxylamine, a UV absorber, a sterically hindered amine, or a mixture thereof.

14. A process for stabilizing an organic polymer against damage by light, oxygen, heat, of a combination thereof, comprising:
adding to or applying to the organic polymer at least one compound according to claim 4.

15. A flame retardant organic polymer comprising the compound of claim 4.

* * * * *